US010251399B2

(12) United States Patent
Jennings

(10) Patent No.: US 10,251,399 B2
(45) Date of Patent: Apr. 9, 2019

(54) LOW-CONCENTRATION PHYTOTOXIC MICRONUTRIENT COMPOUNDS FOR SELECTIVE CONTROL OF INVASIVE PLANT SPECIES

(71) Applicant: Stuart Jennings, Bozeman, MT (US)

(72) Inventor: Stuart Jennings, Bozeman, MT (US)

( * ) Notice: Subject to any disclaimer, the term of this patent is extended or adjusted under 35 U.S.C. 154(b) by 0 days.

(21) Appl. No.: 15/655,004

(22) Filed: Jul. 20, 2017

(65) Prior Publication Data

US 2017/0318815 A1 Nov. 9, 2017

Related U.S. Application Data

(63) Continuation of application No. 14/760,905, filed as application No. PCT/US2014/011690 on Jan. 15, 2014, now Pat. No. 9,775,357, which is a continuation-in-part of application No. 14/038,006, filed on Sep. 26, 2013, now Pat. No. 8,835,355.

(60) Provisional application No. 61/784,778, filed on Mar. 14, 2013, provisional application No. 61/752,605, filed on Jan. 15, 2013, provisional application No. 61/752,681, filed on Jan. 15, 2013.

(51) Int. Cl.
| | | |
|---|---|---|
| *A01N 59/14* | (2006.01) | |
| *A01N 59/20* | (2006.01) | |
| *C05G 3/02* | (2006.01) | |
| *C05D 9/02* | (2006.01) | |

(52) U.S. Cl.
CPC ............ *A01N 59/20* (2013.01); *A01N 59/14* (2013.01); *C05D 9/02* (2013.01); *C05G 3/02* (2013.01); *Y02A 90/40* (2018.01)

(58) Field of Classification Search
None
See application file for complete search history.

(56) References Cited

U.S. PATENT DOCUMENTS

| | | |
|---|---|---|
| 2,544,141 A | 3/1951 | Donleavy |
| 2,618,545 A | 11/1952 | Newcomer |
| 3,034,949 A | 5/1959 | Ryker |
| 2,894,020 A | 7/1959 | McManimie |
| 2,993,923 A | 7/1961 | Warner et al. |
| 3,064,025 A | 11/1962 | Warner et al. |
| 3,429,687 A | 2/1969 | Weil |
| 8,835,355 B2 | 9/2014 | Jennings |
| 9,096,478 B2 | 8/2015 | Jennings |
| 9,775,357 B2 | 10/2017 | Jennings |
| 2014/0200143 A1 | 7/2014 | Jennings |
| 2014/0342911 A1 | 11/2014 | Jennings |
| 2015/0351407 A1 | 12/2015 | Jennings |

FOREIGN PATENT DOCUMENTS

| | | |
|---|---|---|
| DE | 102006033828 | 1/2008 |
| EP | 1563734 A1 | 8/2005 |
| GB | 1 589 362 | 5/1981 |
| JP | H01157904 A | 6/1989 |
| JP | H03264506 A | 11/1991 |
| JP | H05271024 A | 10/1993 |
| JP | 2009-240230 A | 10/2009 |
| NZ | 270128 A | 5/1996 |
| SU | 1634198 | 3/1991 |

OTHER PUBLICATIONS

Silversides (Rate and mode of penetration of herbicides. I. Copper nitrate solutions, Canadian Journal of Agricultural Science (1940), 20, 419-23).*
Hanley et al. (The chemical eradication of lawn weeds, Proc Amer Soc Hort Sci, (1937 (1938)) vol. 35, pp. 845-849).*
Forbes et al. (Copper and other minerals in herbage species and varieties on copper-deficient soils Grass and Forage Science (1981), vol. 36, No. 1, pp. 25-30, 34 refs.).*
Silversides (Rate and mode of penetration of herbicides. I. Copper nitrate solutions, Canadian Journal of Agricultural Science (1940), 20, 419-23) (Year: 1940).*
Hanley et al. (The chemical eradication of lawn weeds, Proc Amer Soc Hort Sci, (1937 (1938)) vol. 35, pp. 845-849) (Year: 1938).*
Forbes et al. (Copper and other minerals in herbage species and varieties on copper-deficient soils Grass and Forage Science (1981), vol. 36, No. 1, pp. 25-30, 34 refs.) (Year: 1981).*
Anonymous, "Weed Killer Made With Borax," http://www.gardenguides.com/102157-weed-killer-made-borax.html (retrieved Mar. 7, 2014).
Choi and Lee, "Micro nutrient toxicity in French marigold." J. Plant Nut. (1996); 19(6): 901-916.
Clifford Collier 1984, Cooperative Extension Service publication 502.
Forbes and Gelman, "Copper and other minerals in herbage species and varieties on copper-deficient soils." Grass and Forage, Science (1981); 36(1): 25-30.
Gardenguides.com skellog Apr. 4, 2008, pp. 1-5.
Hammer, P.A. and D.A. Bailey. "Poinsettia tolerance of molybdenum." HortScience (1987); 22: 1284-1285.
International Search Report PCT Appl. No. PCT/US2014/011690, 6 pages (Jul. 24, 2014).
Kabata-Pendias, A. and Pendias, H. "Trace Elements in Soils and Plants." Third Edition. (2001); CRC Press. pp. 169-179.
Keren, R. and Bingham, F.T., "Boron in water, soils, and plants." Adv. Soil Sci. (1985); 1: 230-276.
Lee, Chiwon W., et al. "Micronutrient Toxicity in Seed Geranium (Pelargonium x hortorum Bailey)." J. Amer. Soc. Hort. Sci. (1996); 121(1): 77-82.
Marousky, F.J. "Symptomology of fluoride and boron injury in Lilium longiflorum." J. Amer. Soc. Hort. Sci. (1981); 106: 341-344.
Partial International Search Report, PCT appl. No. PCT/US2014/011690, 4 pages (Mar. 20, 2014).
Ripa, A.K., et al., "Growing conditions of lawn grasses along highways and recommendations for their creation and maintenance." Latvijas Psr Zinatnu Akademijas Vestis, (1979), No. 7, pp. 110-117.
Skurkhno et al. "Activity of the Rhizosphere of Perennial Leguminous Grasses under Conditions of Biological Agriculture." Russian Agricultural Sciences, 2008, vol. 34, No. 6, pp. 389-392.

* cited by examiner

*Primary Examiner* — Alton N Pryor
(74) *Attorney, Agent, or Firm* — Cooley LLP

(57) ABSTRACT

This invention provides low-dose, low-concentration formulations of phytotoxic trace inorganic compounds for use in methods and systems for selectively and effectively controlling invasive plants.

8 Claims, 17 Drawing Sheets

US 10,251,399 B2

LOW-CONCENTRATION PHYTOTOXIC MICRONUTRIENT COMPOUNDS FOR SELECTIVE CONTROL OF INVASIVE PLANT SPECIES

CROSS-REFERENCE TO RELATED APPLICATIONS

This application claims the benefit of, and is a continuation of U.S. non-provisional application Ser. No. 14/760,905 filed on Jul. 14, 2015, now U.S. Pat. No. 9,775,357, which is a National Stage Entry of International Patent Application No. PCT/US2014/011690, filed on Jan. 15, 2014, which itself is a continuation-in-part of U.S. non-provisional application Ser. No. 14/038,006 filed on Sep. 26, 2013, now U.S. Pat. No. 8,835,355, which claims priority to U.S. provisional application No. 61/784,778 filed on Mar. 14, 2013, U.S. provisional application No. 61/752,605 filed on Jan. 15, 2013, and U.S. provisional application No. 61/752,681 filed on Jan. 15, 2013, each of which is hereby incorporated by reference in its entirely for all purposes. This application is also related to U.S. non-provisional application Ser. No. 14/451,946 filed on Aug. 5, 2014, now U.S. Pat. No. 9,096,478, which claims priority to U.S. non-provisional application Ser. No. 14/038,006 filed on Sep. 26, 2013, now U.S. Pat. No. 8,835,355.

BACKGROUND OF THE INVENTION

Field of Invention

This invention relates to compositions, processes and systems for the control and eradication of invasive plant species (i.e. weeds) (dandelion, spotted knapweed, cheatgrass and others).

Basis for Invention

Invasive weeds are a serious world-wide problem and about 5% of the world economy (~$1.4 T) is spent annually on control. The approach to weed control currently used is ineffective, expensive and causes excessive harm to the environment. The current global practice for weed control involves spraying chemical weed control formulations on the live, above ground tissue of growing plants to selectively disrupt the physiological processes of the plant.

Invasive species are adapted to nutrient-poor soils and out-compete desirable native vegetation once established. As the human population has swelled from 1 B to more than 7 B people over the past 200 years no corner of the globe has been spared from land disturbing activities including grazing, mining, logging, road building, urbanization, and crop production. In many cases land disturbances are severe and native soils have become depleted of nutrients (i.e. disturbed) resulting in a net ecological shift away from soils in geochemical equilibrium with the occupying plant community toward invasive species dominated soils with low fertility.

Plant-soil equilibrium exists through recycling of soil nutrients by decay of above ground biomass. Disequilibrium occurs when the above ground biomass is removed (e.g. heavy grazing or fire) and return of nutrients to the soil greatly reduced. The net condition of global soil is one of declining health and mining of soil nutrients without replacement. Declining soil health, declining plant production and invasion by weeds are the result. Agrarian societies dependent on agriculture output are diminished and made less secure.

In order to address this long-felt need for weed control on disturbed lands, the present invention provides environmentally-friendly, cost-effective compositions, methods and systems for the control of unwanted plants on disturbed soils.

SUMMARY OF THE INVENTION

The present invention provides low-dose, low-concentration formulations of phytotoxic trace inorganic compounds for use in methods and systems to selectively and effectively control invasive plants. According to some embodiments of the present invention, the formulations can be applied as dry products or as a liquid.

According to the present invention, the formulations of the present invention are applicable to selectively and effectively control the germination of invasive plant seed and cause death to emerging invasive plant seedlings and mature plants. Accordingly, advantages compared to conventional methods for control of invasive plants include destruction of seed reserves stored in soil, selectiveness of phytotoxic effect specific to invasive plants, exceptionally low cost per unit area of control, and selective persistence of desirable target species. Trace elements are water-soluble, soil adsorbed, and non-carcinogenic compounds having no known endocrine disruption properties. The present invention takes advantage of the fact that trace inorganic compounds are naturally occurring and required for plant growth as micronutrients. According to the present invention, replacement of adequate quantities of trace elements restores soil health to support desirable plant species and results in the control or eradication of undesirable invasive plants.

The present invention provides methods for controlling the growth of invasive plant species in an existing perennial grass community comprising the steps of applying a micronutrient such as boron or copper to an area of the existing perennial grass community to achieve a soluble boron or copper concentration in the soil of 0.5 milligrams per liter to about 50 milligrams per liter, wherein the growth of the invasive plant species is controlled.

The present invention also provides methods for controlling the growth of invasive plant species in an existing perennial grass community comprising the steps of applying a copper to an area of the existing perennial grass community to achieve a copper concentration in the soil of 250 milligrams per kilogram to about 1400 milligrams per kilogram, wherein the growth of the invasive plant species is controlled.

In some embodiments, the methods and systems of the present invention comprise at least one micronutrient selected from the group consisting of boron, copper, manganese, molybdenum, chloride, zinc compounds, and combinations thereof.

In some embodiments the invasive plant species of the present invention can be one or more of the plants selected from the group consisting of cheatgrass, dandelion, and spotted knapweed.

In some embodiments, the invasive plant species can be any other invasive species affecting a perennial grass community.

In some embodiments, the invasive plant species of the present invention is cheatgrass.

In some embodiments, the boron application produces a soil soluble boron concentration of about 5.0 milligrams per liter to about 15.0 milligrams per liter In some embodiments, the boron applied in the present invention is a boron-containing compound.

In some embodiments, the boron applied in the present invention is a dry product.

In some embodiments, the copper application produces a soil soluble copper concentration of about 0.01 milligrams per liter to about 10 milligrams per liter.

In some embodiments, the copper application produces a soil copper concentration of about 250 milligrams per kilogram to about 1000 milligrams per kilogram.

In some embodiments, the copper applied in the present invention is a copper-containing compound.

In some embodiments, the copper applied in the present invention is a dry product.

In some embodiments, the area of the existing perennial grass community of the present invention is a rangeland or disturbed land.

In some embodiments, of the present invention, the micronutrient is applied prior to germination or to young germinating plants of the invasive species.

In some embodiments, the invention provides methods for controlling the growth of at least one invasive species at a locus to be treated comprising the steps determining an invasive plant species to be controlled in an existing perennial grass community, measuring the soluble boron or copper concentrations in the soil of the existing perennial grass community, and applying boron or copper to an area of the existing perennial grass community to achieve a soluble boron or copper concentration in the soil of the existing perennial grass community from about 0.5 milligrams per liter to about 50 milligrams per liter.

In some embodiments of the present invention, the uppermost about 1 inch of soil achieves a soluble boron concentration of 0.5 milligrams per liter to about 50 milligrams per liter. In some embodiments of the present invention, the uppermost about 1 inch of soil achieves a soluble copper concentration of 0.5 milligrams per liter to about 50 milligrams per liter.

In some embodiments, the present invention provides for methods for controlling the growth of invasive plant species in an existing perennial grass community comprising the steps of applying boron or copper micronutrients to an area of the existing perennial grass community to achieve a soluble boron or copper concentration in the soil of the existing perennial grass community from about 0.5 milligrams per liter to about 50 milligrams per liter in the uppermost about 1 inch of soil.

In some embodiments, the invention provides methods for controlling the growth of at least one invasive species at a locus to be treated comprising the steps determining an invasive plant species to be controlled in an existing perennial grass community, measuring the copper concentrations in the soil of the existing perennial grass community, and applying copper to an area of the existing perennial grass community to achieve a copper concentration in the soil of the existing perennial grass community from about 250 milligrams per kilogram to about 1400 milligrams per kilogram.

In some embodiments of the present invention, the uppermost about 1 inch of soil achieves a copper concentration of 250 milligrams per kilogram to about 1400 milligrams per kilogram.

In some embodiments, the present invention provides for methods for controlling the growth of invasive plant species in an existing perennial grass community comprising the steps of applying copper to an area of the existing perennial grass community to achieve a copper concentration in the soil of the existing perennial grass community from about 250 milligrams per kilogram to about 1400 milligrams per kilogram in the uppermost about 1 inch of soil.

In some embodiments, the application of boron or copper micronutrients to a locus kills invasive species, but does not kill desirable perennial grass communities.

In some embodiments, the present invention teaches methods of preserving or increasing the vigor of a native perennial grass community while selectively controlling invasive species.

In some embodiments, the invasive species are annual invasive species.

In some embodiments, the present invention provides for methods of preserving or increasing the vigor of an existing native perennial grass community, comprising the steps of: applying boron or copper micronutrients to an area of the existing native perennial grass community to achieve a soluble boron or copper concentration in the soil of the existing native perennial grass community from about 0.5 milligrams per liter to about 50 milligrams per liter in the uppermost about 1 inch of soil, wherein said method preferentially controls non-native invasive species present in the area, while simultaneously promoting the growth of native perennial species. In some embodiments, the aforementioned method preferentially controls annual non-native invasive species. In other embodiments, the aforementioned method preferentially controls perennial non-native invasive species. The aforementioned method may also be used to preserve or increase the vigor of an existing native annual grass community.

In particular aspects, invasive cheatgrass is preferentially controlled in a native perennial grass community, wherein the health of the cheatgrass is decreased relative to the health of the native perennial grass community. Thus, the cheatgrass is preferentially selected against, or controlled, relative to the native perennial grass assemblage.

In some embodiments, the boron or copper applied to the plant assemblages is not present in a commercial fertilizer composition.

In some embodiments, the boron applied to the plant assemblages is not a fluoborate composition.

In some embodiments, the boron applied to the plant assemblages is not borax.

In some embodiments, the active ingredient applied in the disclosed methods consists essentially of boron, wherein said boron is essentially free of other ingredients. Thus, in some aspects, the boron is applied in compositions, wherein any other potentially active compound is present in the composition, if at all, in only de minimis trace amounts. Consequently, compositions that contain more than trace amounts of boron, e.g. some commercial fertilizers, are excluded from certain embodiments of the disclosed methods.

In certain embodiments, the present method applies boron or copper to plant assemblages prior to germination of an invasive annual species that is to be controlled. In some aspects, boron or copper is applied before germination of cheatgrass seeds.

Thus, in certain embodiments, the methods taught herein are able to selectively increase the vigor of a native perennial plant assemblage, by causing interfering effects to the germination of non-native invasive annual seedlings.

In some embodiments, the methods and systems of the present invention use aqueous solutions which also include liquid water.

In some embodiments of the present invention, the locus to be treated is selected from the group consisting of disturbed land, urban land, rangeland, forestland, roadside, brownfield and cultivated land.

In some embodiments of the present invention, the locus to be treated comprises invasive plant species selected from the group consisting of live plants on the soil surface, seed, senesced seed-bearing plants, and live seed-bearing plants.

The present invention also provides methods and systems of controlling the growth of invasive plant species comprising the steps of applying from about 0.5 to about 20 pounds of at least one water soluble micronutrient per acre as a dry product to a locus to be treated.

In some embodiments of the present invention, the at least one water soluble micronutrient is selected from the group consisting of boron, copper, manganese, molybdenum, chloride or zinc compounds, or combinations thereof.

In some embodiments, the methods and systems of the present invention for controlling the growth of at least one invasive plant species at a locus to be treated involve determining an invasive plant species to be controlled at the locus to be treated; measuring the soluble micronutrient concentrations in soil at the locus to be treated; determining at least one micronutrient to be applied to control the invasive plant species; and applying the at least one micronutrient to the locus to be treated to achieve a growth controlling effective soluble concentration of the at least one micronutrient in the soil at the locus to be treated.

In some embodiments, the methods and systems of the present invention are used to prevent growth of invasive plant species by applying at least one micronutrient to an area to be treated to achieve a soluble micronutrient concentration in soil of the area to be treated of from about 0.5 milligrams to about 50 milligrams per liter.

In some embodiments, the methods and systems of the present invention prevent plant growth on an area to be treated by applying a toxic amount of at least one micronutrient to the area to be treated.

All patents, patent applications, provisional patent applications and publications referred to or cited herein, are incorporated by reference in their entirety to the extent they are not inconsistent with the teachings of the specification.

DETAILED DESCRIPTION OF INVENTION

Figure 1A:
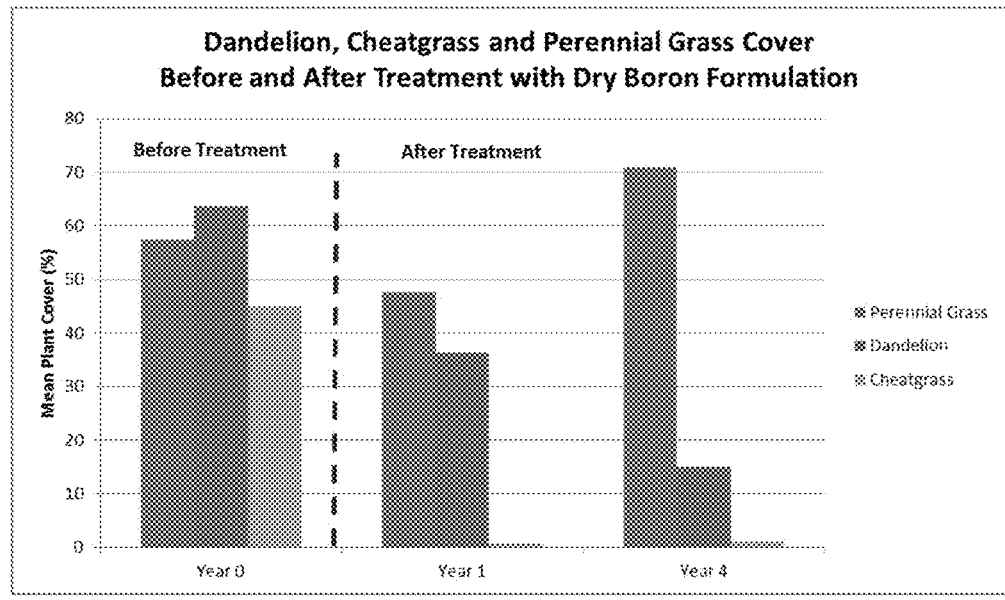
FIG. 1A illustrates the percent mean plant cover of dandelion (*Taraxacum officinale*), cheatgrass (*Bromus tectorum*) and perennial grass (several species) over a 5 year time period following application of dry formulations of varying boron concentrations at a field site in Belgrade, Mont.

Invasive plants (i.e. weeds) are well established across the globe and contribute to economic losses, habitat degradation, losses in land productivity and value. Weeds have become established through a variety of landscape changes including, but not limited to, fire, grazing, land clearing, tillage, urbanization, and other land disturbing activities. Weed seeds have also traveled the globe becoming established as exotic species on continents on opposite sides of the world. Many of the noxious weeds found in the U.S. evolved naturally elsewhere and become established and proliferate in the absence of natural controls.

Billions of dollars are spent annually controlling weeds. The Nature Conservancy Global Invasive Species Team reports world-wide damage from invasive species amounts to $1.4 trillion annually, or five percent of the global economy (Pimentel et al. 2001). In the U.S. impacts from invasive amount to $120 billion annually with more than 100 million acres affected (Pimental et al. 2005). Leafy spurge (*Euphorbia esula*) infestations in the northern Great Plains costs ranchers $120 million annually (Bangsund et al. 1991).

Herbicides are the principal strategy for controlling weeds including Synthetic formulations such as glyphosate (ROUNDUP®/Monsanto, and others), PLATEAU® (imazapic, BASF), JOURNEY® (imazapic+glyphosate, BASF), MATRIX® (sulfonylurea, DuPont), LANDMARK XP® (sulfometuron and chlorsulfuron, Dupont), OUST® (sulfometuron, DuPont) and other formulations are sold to control weeds. Effectiveness of conventional herbicide applications is highly dependent on timing of herbicide application relative to both plant physiology/growth stage, specific contact with growing vegetation, and complimenting rainfall conditions. The cost of chemical control can be as high as $250 per acre or greater with repeated applications. Land managers often rule out the use of herbicides for control of weeds due to high cost, low effectiveness and damage to desirable species. Effective weed control methods which do not harm desirable species are available, but often have limitations related to cost, need for repeated application and a general concern for the hazards associated with the application of organic chemicals in the environment. Most herbicides used for control of invasive species are organic liquid chemicals applied to the leaf tissue which result in disruption of plant metabolic processes. These same organic chemicals are not naturally-derived and may be harmful to water quality, wildlife and humans. Additionally, research suggests that some invasive plant species are developing resistance to herbicides (Maxwell et al. 1990; Heap 2006) and the herbicide in most widespread use across the world (i.e. glyphosate) may cause unintended consequences including limiting micronutrient availability (Yamada et al. 2009), as well as broad endocrine disruption.

Of the sixteen chemical elements known to be important to a plant's growth and survival, thirteen come from the soil, are dissolved in water and absorbed through a plant's root system. In some instances, there are insufficient levels of these elements to sustain normal plant growth and development. Agriculturalists rely on the application of fertilizer to ameliorate elemental nutritional deficiencies, with the expectation of a positive, 'desirable' plant response to the added nutrient. It is known that all plant species have definable nutrient requirements and many plant species have unique sensitivities to trace elements, otherwise known as micro-nutrients. Some combinations and concentrations of these nutrients, particularly the micronutrients, can be detrimental or toxic to some plants. Sensitivities to low or high micro-nutrient levels can be expressed in plants as depressed or stunted growth, delayed maturity, incomplete physiological development, cell necrosis, or premature death (Kabata-Pendias and Pendias, 2001). The range of micronutrients required for optimal plant growth for each species may be broad or narrow. Soils have unique geochemical characteristics related to climate and parent material. Native plant communities have adapted to these unique conditions over thousands of years. Under natural conditions these plant-soil systems maintain an equilibrium level of nutrient availability until disturbed by natural or anthropogenic forces causing a geochemical disequilibrium which makes these plant-soil systems susceptible to invasive species colonization.

Phytotoxic levels of trace elements in soils are known to occur naturally. Acid-sulfate soil systems are known to mobilize metals resulting in phytotoxic soil conditions for plant species not tolerant of soil acidity. Saline soil conditions are also known to occur in arid climates resulting in phytotoxic conditions for plant species not tolerant of elevated salinity. Anthropogenic releases of contaminants to the natural environment are also known to cause phytotoxic soil conditions. Mining and smelting are both known to cause acidic and metalliferous soil conditions, while agricultural practices such as fallow farming may lead to salinization of the soil resource.

Farmers may add fertilizers or soil amendments to increase the yield of crops and overcome any geochemical limitations of the soil which affects crop yield. The plant macronutrients nitrogen, phosphorous and potassium are routinely added to soil to maximize yield. In some cases trace elements such as copper, zinc or boron may be added to the soil if the crop grown has unique trace element fertilization needs for maximum yield. Farmers may also add soil amendments such as lime ($CaCO_3$) to control soil acidity. Similarly, land reclamation scientists may add soil amendments and fertilizers to control undesirable soil geochemistry at disturbed sites. Seeding of plant species which are tolerant of site-specific conditions is also a common practice for revegetation of disturbed sites.

According to the present invention, minute concentrations of the plant micro-nutrients boron, copper, zinc, manganese, chlorine and molybdenum when applied to the soil, directly to weed seed, or to soil containing weed seed, result in seed death, failure of weed seed to germinate, and pre-mature mortality of emerging seedlings through micro-nutrient induced phytotoxicity. According to the present invention, soil conditions phytotoxic to weed species yet not phytotoxic to desirable plant species are made possible through knowledge of the dose-response curve for each unique micronutrient-plant interaction. The resulting modified geochemical soil conditions cause selective phytotoxic control of invasive plant species while allowing establishment and persistence of desirable plant species. Timing of application of the micro-nutrient is targeted to elevate soluble soil micronutrient concentrations in soil containing weed seed prior to seed germination. Thus, micro-nutrient application can be made any time following weed seed drop and before weed seed germination. The timing of micronutrient application is unique to the invasive species targeted and its growth cycle. Fundamentally, the elevated soil micronutrient conditions must exist while the plant is actively growing (whether seed is germinating below the soil surface or producing leaf tissue above the soil surface). The period of micronutrient application may encompass the entire calendar year, depending on the plant species and site conditions including composition of desirable plant species present.

According to the present invention, mature growing invasive species can be controlled by micronutrient addition. For example, weeds commonly grow to maturity early in the growing season and may produce and drop seed in late-spring to mid-summer. Selective control of invasive plant species by applied inorganic micro-nutrient-induced phytotoxicity has not been previously reported in the scientific literature. Organic chemical herbicides for control of invasive species are known. Phytotoxicity to plants due to micronutrient imbalances are known. However, prior to the present invention, the selective control of invasive species described herein by micro-nutrient induced phytotoxicity in the soil has not been previously reduced to practice.

According to one exemplary embodiment the present invention, the micronutrient boron is used to illustrate the plant response of two representative desirable plant species (bluebunch wheatgrass and Kentucky bluegrass) and three representative invasive plant species (cheatgrass, dandelion and spotted knapweed). As used herein, the phrases "desirable plant species" and "desirable plants" refer to plants that are present in a specific location where they are wanted. As used herein, the phrases "invasive plant species" and "invasive plants" refer to plants that are present in a specific location where they are unwanted. Thus, according to the present invention, whether a plant is considered a desirable or an invasive plant in a particular situation depends on the specific location involved and the desires of the manager or owner of that location. For example, a certain grass species may be considered a desirable plant in a mixed alfalfa/grass field used for forage production or livestock grazing. That same grass species, however, may be considered an invasive plant in an alfalfa field to be used for certified alfalfa seed production. In the latter situation, the grass species would be classified a weed and if too many seeds or other parts of the grass species were harvested with the alfalfa seed that may result in the seed from that alfalfa production field being denied certification. On an un-tilled landscape occupied by native vegetation the colonization of the site by non-native or exotic plants is illustrative in that the native vegetation would be the "desirable species" and the non-native and exotic colonizing species would be an "invasive species".

According to other embodiments of the present invention, the control of invasive plant species shown herein by using various boron solutions is also applicable and demonstrated using other micronutrients and other species and combinations of species. This disclosure is not intended to be limited to the invasive species provided as examples. A partial list of known invasive species would include, but not be limited to: cheatgrass, dandelion, knapweeds (spotted, diffuse, Russian), bindweed, chickweed, ground ivy, Canada thistle, burdock, houndstongue, yellow star thistle, Himalayan bush clover (lespedeza), privet, Russian thistle, kochia, halogeton, Japanese knotweed, leafy spurge, St. Johnswort, toadflax (yellow and Dalmation), tansy, whitetop, hawkweed, cinquefoil, ox-eye daisy and others either known to be a problematic invasive species and also those not yet determined to be such.

Cheatgrass, a non-native, invasive, Euro-Asian winter annual grass species, is present or dominant on some 100 million acres in the Great Basin and Intermountain West. Several thousand new acres are invaded by cheatgrass every day, with each plant producing upwards of 1,000 seeds. Cheatgrass is a principal driving force behind epidemic wildfires occurring continually and with greater frequency across the western U.S. and is largely responsible for decline of the sagebrush-steppe ecosystem, home to more than 1500 species of birds, vertebrate, and invertebrate species including iconic western ungulates deer, elk, antelope, and the endangered sage grouse; all of which are dependent on the habitat and health of this rapidly declining ecosystem. Thus, in one embodiment, the present invention provides a method for soil application of a low-concentration liquid spray mixture of boric acid, sodium borate, sodium tetraborate, or disodium tetraborate, or other soluble sources of boron, applied to field sites to control cheatgrass and other non-desirable annual grass species.

This invention demonstrates that fertilization by micronutrients is selectively harmful to invasive plants while desirable species are either stimulated or tolerant of the same levels shown to be phytotoxic to the weedy species. This makes ecological sense as later successional plant communities have more highly evolved nutrient cycling and elevated levels of fertility. The desirable plants characteristic of the late successional plant communities are tolerant and benefit from higher levels of soil fertility and especially adequate amounts of trace elements (also known as micronutrients). Invasive species are intolerant of elevated micronutrient levels and thrive in low nutrient soils. The recycling of trace elements by later successional plant communities may have been a primary natural control on preventing weed invasion. Upon disturbance and loss of pre-disturbance fertility native plant communities become susceptible to weed invasion. The recovery of these systems through natural soil building and plant succession is likely to occur over long periods of time (hundreds to thousands of years) absent repeated disturbance. Consider a logging road built through a mountain meadow. The predisturbance desirable diverse vegetation exists on both sides of the road while the road bed and cut/fill slopes become colonized by invasive species. Of relevance to the invention is that while the invasives produce large amounts of seed that fall on the adjacent mountain meadow they fail to become established. Trace element phytotoxicity to such weed seeds is an important control on the invasion of weedy species such as dandelions beyond the road bed. In this invention soil health of disturbed lands is restored by reverse engineering the inorganic trace element/micronutrient fingerprint of the predisturbance soil and soil micronutrients are added resulting in the phytotoxic control of invasive plant species.

According to the present invention, any micronutrient fertilizer may be used, applied alone or in combination with other micronutrients, or even in combination with macronutrients such as nitrogen, phosphorous, and potassium. Central to this invention is the discovery that weeds are negatively impacted by small quantities of micronutrients whereas more desirable species (perennial grasses, native forbs) are tolerant of these same levels. The present invention demonstrates that there is a differential tolerance between invasives and desirable plants. For example, consider the micronutrient copper, its total elemental amount in a given soil might be 50 mg/Kg with maybe 0.1% plant available copper in any given year. If inputs and outputs of copper are in balance, the total amount of copper remains at 50 mg/Kg and the plant available amount remain at 0.1% of the total. In the example of overgrazing, copper translocated to the above ground biomass is removed from the system and micronutrient recycling to the soil is disrupted. Over time the total amount of copper in the soil begins to decline to <50 mg/Kg, but more significantly the plant available amount of copper sharply declines (the total elemental amount is attributable to geologic materials and is often very slowly weathered to plant available forms). For the sake of this example (and in parallel with observations supporting this invention), let's say that weeds are not tolerant of more than 0.1% plant available copper. If that level drops due to overgrazing to say 0.01% plant available copper the site would likely become colonized by invasive plants if an invasive plant species seed source is nearby. In this invention, fertilizing the soil to restore the pre-disturbance plant available copper level (target of 0.1%) would result in reduction or elimination of weeds and reestablishment of more desirable plant species either through natural recolonization or reseeding. The copper fertilizer to be used could be applied as one of several compounds such as shown in Table 1. Fertilizer micronutrient formulations are highly soluble compared to geological mineral sources in the natural soil.

TABLE 1

Fertilizer sources of copper.

| Source | Formula | Percent Copper |
|---|---|---|
| Copper chelate | $Na_2CuEDTA$ | 13 |
| Copper sulfate | $CuSO_4 \cdot 5H_2O$ | 25 |
| Cupric oxide | $CuO$ | 75 |
| Cuprous oxide | $Cu_2O$ | 89 |

According to the present invention, in order to calculate the rate of a micronutrient fertilizer that may be applied, following are several calculations based on the above table. If one wanted to add 10 pounds of plant available copper per acre using copper chelate fertilizer you would apply 76.9 pounds of copper chelate per acre since the fertilizer is only 13% copper. Similarly, for the same amount of plant available copper per acre using copper sulfate, one would apply 40 pounds of fertilizer per acre as copper sulfate, or 13 pounds of cupric oxide per acre, or 11.2 pounds of cuprous oxide per acre. Any copper containing fertilizer source could be used to provide the plant available copper. Similar calculations would apply to any other micronutrient being applied at a target rate reflecting the percentage of the micronutrient in each unique fertilizer compound.

Whether the formulation is applied as a dry formula or as a liquid formula is irrelevant as the objective is to achieve the desired amount of fertilization in the soil to favor the species desired and reduce or eliminate the invasive weedy species. The products described in Table 1 are dry and could be applied to the soil surface in the dry form with a tractor/spreader. The dry fertilizer would become available to the plant upon rainfall or snowmelt. Conversely, the products could be dissolved in water and applied with a sprayer as long as the application rates are appropriate to achieve the desired fertility goal. The products could be dissolved in any liquid not harmful to plants and applied as the liquid is only the carrier to achieve the loading rate.

Thus, in some embodiments of the present invention, copper micronutrient is applied to a locus to achieve copper soil concentration ranges as follows (including any/all concentrations between these ranges): 1-25 mg/Kg, 25-50 mg/Kg, 50-75 mg/Kg, 75-100 mg/Kg, 100-125 mg/Kg, 125-150 mg/Kg, 150-175 mg/Kg, 175-200 mg/Kg, 200-225 mg/Kg, 225-250 mg/Kg, 250-275 mg/Kg, 275-300 mg/Kg, 300-325 mg/Kg, 325-350 mg/Kg, 350-375 mg/Kg, 375-400 mg/Kg, 400-425 mg/Kg, 425-450 mg/Kg, 450-475 mg/Kg, 475-500 mg/Kg, 500-525 mg/Kg, 525-550 mg/Kg, 550-575 mg/Kg, 575-600 mg/Kg, 600-625 mg/Kg, 625-650 mg/Kg, 650-675 mg/Kg, 675-700 mg/Kg, 700-725 mg/Kg, 725-750 mg/Kg, 750-775 mg/Kg, 775-800 mg/Kg, 800-825 mg/Kg, 825-850 mg/Kg, 850-875 mg/Kg, 875-900 mg/Kg, 900-925 mg/Kg, 925-950 mg/Kg, 950-975 mg/Kg, 975-1000 mg/Kg, 1000-1025 mg/Kg, 1025-1050 mg/Kg, 1050-1075 mg/Kg, 1075-1100 mg/Kg, 1100-1125 mg/Kg, 1125-1150 mg/Kg, 1150-1175 mg/Kg, 1175-1200 mg/Kg, 1200-1225 mg/Kg, 1225-1250 mg/Kg, 1250-1275 mg/Kg, 1275-1300 mg/Kg, 1300-1325 mg/Kg, 1325-1350 mg/Kg, 1350-1375 mg/Kg, 1375-1400 mg/Kg, 1400-1425 mg/Kg, 1425-1450 mg/Kg, 1450-1475 mg/Kg, 1475-1500 mg/Kg, 1500-1525 mg/Kg, 1525-1550 mg/Kg, 1550-1575 mg/Kg, 1575-1600 mg/Kg, 1600-1625 mg/Kg, 1625-1650 mg/Kg, 1650-1675 mg/Kg, 1675-1700 mg/Kg, 1700-1725 mg/Kg, 1725-1750 mg/Kg, 1750-1775 mg/Kg, 1775-1800 mg/Kg, 1800-1825 mg/Kg, 1825-1850 mg/Kg, 1850-1875 mg/Kg, 1875-1900 mg/Kg, 1900-1925 mg/Kg, 1925-1950 mg/Kg, 1950-1975 mg/Kg, 1975-2000 mg/Kg, 2000-2025 mg/Kg, 2025-2050 mg/Kg, 2050-2075 mg/Kg, 2075-2100 mg/Kg, 2100-2125 mg/Kg, 2125-2150 mg/Kg, 2150-2175 mg/Kg, 2175-2200 mg/Kg, 2200-2225 mg/Kg, 2225-2250 mg/Kg, 2250-2275 mg/Kg, 2275-2300 mg/Kg, 2300-2325 mg/Kg, 2325-2350 mg/Kg, 2350-2375 mg/Kg, 2375-2400 mg/Kg, 2400-2425 mg/Kg, 2425-2450 mg/Kg, 2450-2475 mg/Kg, 2475-2500 mg/Kg, 2500-2525 mg/Kg, 2525-2550 mg/Kg, 2550-2575 mg/Kg, 2575-2600 mg/Kg, 2600-2625 mg/Kg, 2625-2650 mg/Kg, 2650-2675 mg/Kg, 2675-2700 mg/Kg, 2700-2725 mg/Kg, 2725-2750 mg/Kg, 2750-2775 mg/Kg, 2775-2800 mg/Kg, 2800-2825 mg/Kg, 2825-2850 mg/Kg, 2850-2875 mg/Kg, 2875-2900 mg/Kg, 2900-2925 mg/Kg, 2925-2950 mg/Kg, 2950-2975, and 2975-3000 milligrams of copper per kilogram of soil. In other embodiments of the present invention, copper micronutrient is applied to a locus to achieve a soil copper concentration of about: 25 mg/Kg, 50 mg/Kg, 75 mg/Kg, 100 mg/Kg, 125 mg/Kg, 150 mg/Kg, 175 mg/Kg, 200 mg/Kg, 225 mg/Kg, 250 mg/Kg, 275 mg/Kg, 300 mg/Kg, 325 mg/Kg, 350 mg/Kg, 375 mg/Kg, 400 mg/Kg, 425 mg/Kg, 450 mg/Kg, 475 mg/Kg, 500 mg/Kg, 525 mg/Kg, 550 mg/Kg, 575 mg/Kg, 600 mg/Kg, 625 mg/Kg, 650 mg/Kg, 675 mg/Kg, 700 mg/Kg, 725 mg/Kg, 750 mg/Kg, 775 mg/Kg, 800 mg/Kg, 825 mg/Kg, 850 mg/Kg, 875 mg/Kg, 900 mg/Kg, 925 mg/Kg, 950 mg/Kg, 975 mg/Kg, 1000 mg/Kg, 1025 mg/Kg, 1050 mg/Kg, 1075 mg/Kg, 1100 mg/Kg, 1125 mg/Kg, 1150 mg/Kg, 1175 mg/Kg, 1200 mg/Kg, 1225 mg/Kg, 1250 mg/Kg, 1275 mg/Kg, 1300 mg/Kg, 1325 mg/Kg, 1350 mg/Kg, 1375 mg/Kg, 1400 mg/Kg, 1425 mg/Kg, 1450 mg/Kg, 1475 mg/Kg, 1500 mg/Kg, 1525 mg/Kg, 1550 mg/Kg, 1575 mg/Kg, 1600 mg/Kg, 1625 mg/Kg, 1650 mg/Kg, 1675 mg/Kg, 1700 mg/Kg, 1725 mg/Kg, 1750 mg/Kg, 1775 mg/Kg, 1800 mg/Kg, 1825 mg/Kg, 1850 mg/Kg, 1875 mg/Kg, 1900 mg/Kg, 1925 mg/Kg, 1950 mg/Kg, 1975 mg/Kg, 2000 mg/Kg, 2025 mg/Kg, 2050 mg/Kg, 2075 mg/Kg, 2100 mg/Kg, 2125 mg/Kg, 2150 mg/Kg, 2175 mg/Kg, 2200 mg/Kg, 2225 mg/Kg, 2250 mg/Kg, 2275 mg/Kg, 2300 mg/Kg, 2325 mg/Kg, 2350 mg/Kg, 2375 mg/Kg, 2400 mg/Kg, 2425 mg/Kg, 2450 mg/Kg, 2475 mg/Kg, 2500 mg/Kg, 2525 mg/Kg, 2550 mg/Kg, 2575 mg/Kg, 2600 mg/Kg, 2625 mg/Kg, 2650 mg/Kg, 2675 mg/Kg, 2700 mg/Kg, 2725 mg/Kg, 2750 mg/Kg, 2775 mg/Kg, 2800 mg/Kg, 2825 mg/Kg, 2850 mg/Kg, 2875 mg/Kg, 2900 mg/Kg, 2925 mg/Kg, 2950 mg/Kg, 2975 mg/Kg, and 3000 milligrams of copper per kilogram of soil.

Copper compounds vary in solubility. Therefore, the plant-available amounts of copper will vary in the soil in accordance to the mineral form of copper and their respective solubility. For example, copper fertilizers might be as much as 50% soluble while copper fallout from a smelter might be less than 1% soluble. Likewise, soil acidity is an important control on copper solubility. For a given total elemental amount of copper, the plant availability (solubility) may vary by orders of magnitude in accordance with the soil pH.

Thus, in some embodiments of the present invention, copper or other micronutrients are applied to a locus to achieve a soluble copper soil concentration of about: 0.01 mg/L, 0.02 mg/L, 0.03 mg/L, 0.04 mg/L, 0.05 mg/L, 0.06 mg/L, 0.07 mg/L, 0.08 mg/L, 0.09 mg/L, 0.10 mg/L, 0.15 mg/L, 0.20 mg/L, 0.25 mg/L, 0.30 mg/L, 0.35 mg/L, 0.40 mg/L, 0.45 mg/L, 0.50 mg/L, 0.55 mg/L, 0.60 mg/L, 0.65 mg/L, 0.70 mg/L, 0.75 mg/L, 0.80 mg/L, 0.85 mg/L, 0.90 mg/L, 0.95 mg/L, 1.00 mg/L, 1.50 mg/L, 2.00 mg/L, 2.50 mg/L, 3.00 mg/L, 3.50 mg/L, 4.00 mg/L, 4.50 mg/L, 5.00 mg/L, 5.50 mg/L, 6.00 mg/L, 6.50 mg/L, 7.00 mg/L, 7.50 mg/L, 8.00 mg/L, 8.50 mg/L, 9.00 mg/L, 9.50 mg/L, 10.00 mg/L, 11.00 mg/L, 12.00 mg/L, 13.00 mg/L, 14.00 mg/L, 15.00 mg/L, 16.00 mg/L, 17.00 mg/L, 18.00 mg/L, 19.00 mg/L, 20.00 mg/L, 21.00 mg/L, 22.00 mg/L, 23.00 mg/L, 24.00 mg/L, 25.00 mg/L, 26.00 mg/L, 27.00 mg/L, 28.00 mg/L, 29.00 mg/L, 30.00 mg/L, 31.00 mg/L, 32.00 mg/L, 33.00 mg/L, 34.00 mg/L, 35.00 mg/L, 36.00 mg/L, 37.00 mg/L, 38.00 mg/L, 39.00 mg/L, 40.00 mg/L, 41.00 mg/L, 42.00 mg/L, 43.00 mg/L, 44.00 mg/L, 45.00 mg/L, 46.00 mg/L, 47.00 mg/L, 48.00 mg/L, 49.00 mg/L, and 50.00 milligrams per liter of soil.

In other embodiments of the present invention, copper or other micronutrients are applied to a locus to achieve soluble copper soil concentration ranges as follows (including any/all concentrations between these ranges): 0.01-0.02 mg/L, 0.02-0.03 mg/L, 0.03-0.04 mg/L, 0.04-0.05 mg/L, 0.05-0.06 mg/L, 0.06-0.07 mg/L, 0.07-0.08 mg/L, 0.08-0.09 mg/L, 0.09-0.10 mg/L, 0.10-0.15 mg/L, 0.15-0.20 mg/L, 0.20-0.25 mg/L, 0.25-0.30 mg/L, 0.30-0.35 mg/L, 0.35-0.40 mg/L, 0.40-0.45 mg/L, 0.45-0.50 mg/L, 0.50-0.55 mg/L, 0.55-0.60 mg/L, 0.60-0.65 mg/L, 0.65-0.70 mg/L, 0.70-0.75 mg/L, 0.75-0.80 mg/L, 0.80-0.85 mg/L, 0.85-0.90 mg/L, 0.90-0.95 mg/L, 0.95-1.00 mg/L, 1.00-1.50 mg/L, 1.50-2.00 mg/L, 2.00-2.50 mg/L, 2.50-3.00 mg/L, 3.00-3.50 mg/L, 3.50-4.00 mg/L, 4.00-4.50 mg/L, 4.50-5.00 mg/L, 5.00-5.50 mg/L, 5.50-6.00 mg/L, 6.00-6.50 mg/L, 6.50-7.00 mg/L, 7.00-7.50 mg/L, 7.50-8.0 mg/L, 8.00-8.50 mg/L, 8.50-9.0 mg/L, 9.00-9.50 mg/L, 9.50-10.00 mg/L, 10.00-10.50 mg/L, 10.50-11.00 mg/L, 11.00-11.50 mg/L, 11.50-12.00 mg/L, 12.00-13.00 mg/L, 13.00-14.00 mg/L, 14.00-15.00 mg/L, 15.00-16.00 mg/L, 16.00-17.00 mg/L, 17.00-18.00 mg/L, 18.00-19.00 mg/L, 19.00-20.00 mg/L, 20.00-21.00 mg/L, 21.00-22.00 mg/L, 22.00-23.00 mg/L, 23.00-24.00 mg/L, 24.00-25.00 mg/L, 25.00-26.00 mg/L, 26.00-27.00 mg/L, 27.00-28.00 mg/L, 28.00-29.00 mg/L, 29.00-30.00 mg/L, 30.00-31.00 mg/L, 31.00-32.00 mg/L, 32.00-33.00 mg/L, 33.00-34.00 mg/L, 34.00-35.00 mg/L, 35.00-36.00 mg/L, 36.00-37.00 mg/L, 37.00-38.00 mg/L, 38.00-39.00 mg/L, 39.00-40.00 mg/L, 40.00-41.00 mg/L, 41.00-42.00 mg/L, 42.00-43.00 mg/L, 43.00-44.00 mg/L, 44.00-45.00 mg/L, 45.00-46.00 mg/L, 46.00-47.00 mg/L, 47.00-48.00 mg/L, 48.00-49.00 mg/L, and 49.00-50.00 milligrams per liter of soil.

In one aspect, this invention is fundamentally about mass balance—restoring appropriate amounts of soil micronutrients in soil by replacing micronutrients lost due to land disturbance. According to the present invention, the consequences of restoring pre-disturbance levels of soil micronutrients include making the soil inhospitable to invasive species.

In another aspect, this invention is about a hypothesis and careful observation of the differential sensitivities of weeds compared to more desirable species to micronutrients.

How much micronutrient fertilizer to add is a function of the existing amount of micronutrients in the soil and the specific weedy and specific desirable plant species present at a site on which the invention is to be practiced. The amount of micronutrients present in a disturbed soil is a unique quantity that can be measured by laboratory analysis. Geologic parent material, soil formation history, land use history, climate and other factors influence the elemental levels of all inorganic constituents in the soil. The process to determine the specific micronutrients and amounts of each to be applied involves collecting samples of soil from at least two representative areas or sites: at least one sample from an undisturbed portion of the site with desirable plant species and at least one sample from a disturbed portion of the site with invasive plant species and diminished desirable plant species cover. The difference in soil micronutrient levels between the "good" site and "bad" site form the basis for calculation of fertilizer application rates. The amount of micronutrient fertilizer added is the difference between the degraded site with low fertility and the reference site with natural levels of soil fertility. According to the present invention, site specific fertilizer prescription can be developed and applied. In larger landscapes with common soil and vegetation characteristics generalized micronutrient application strategies may be applicable to representative areas. Also when undisturbed sites cannot be found on the larger landscape, generalized micronutrient application may be required to control the targeted invasive species.

Plant micronutrient levels in soil are generally very low (roughly a few pounds per acre of a given plant available micronutrient). Correspondingly, the amount of micronutrient fertilizer to be added per acre would also be low and dependent on the elemental levels of micronutrient in the fertilizer to be applied. In the case where fertilizer is impractical to apply at low rates (a few pounds per acre) due to the difficulty of applying a thin uniform amount of fertilizer using mechanical equipment, the fertilizer can be bulked up to add weight and/or volume to aid in spreading. Bulking of fertilizer can be accomplished using sand, rice hulls, corn meal, sawdust, crushed walnut shells, corn stover or equivalent. For example if the target fertilizer application rate was 5 pounds per acre and the reasonable minimum application rate with a given piece of equipment was 10 pounds per acre an additional 5 pounds of bulking material could be added to the 5 pounds of fertilizer (the active ingredient).

Figure 9:
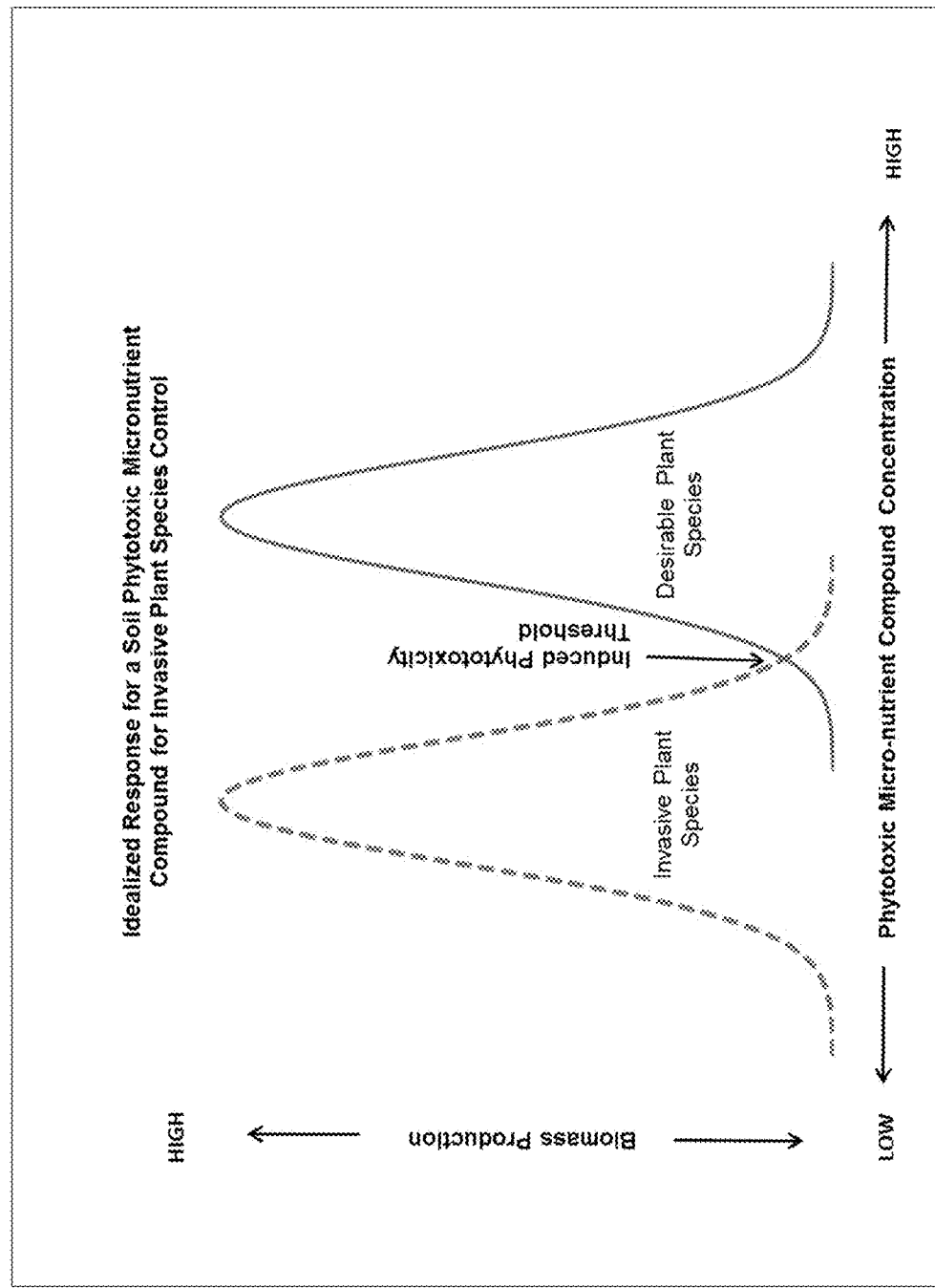
FIG. 9. Illustrates an idealized invasive species and desirable plant species wherein the invasive species is less tolerant of increasing soil micro-nutrient compounds compared to the desirable plant species. The Induced Phytotoxicity Threshold (IPT) shown constitutes the target level for micro-nutrient addition to the soil to cause phytotoxic control of the invasive plant species while causing no harm to the desirable plant species.

A second factor affecting the amount of fertilizer to be added is the plant species present—both desirable and invasive. In this invention it is recognized that each plant species has a unique trace element requirement: too little of a given micronutrient and the plant is deficient, too much of a given micronutrient and the plant experiences phytotoxicity. In making this invention, I have observed that invasive species have lower tolerance to a given soil micronutrient concentration compared to desirable plant species (typically perennial grasses). See, e.g., FIG. 9. It is this differential sensitivity to micronutrients in the soil shown by desirable plants compared to invasive plant species that is fundamental to the invention. The application of this technology will establish the levels of one or more micronutrients above phytotoxic levels for invasive plant species and below levels harmful to desirable species for a given site. All data collected to date have shown that perennial grass species are much more tolerant of elevated micronutrient levels compared to weeds. This information is not known in the scientific literature, nor is the control of invasive species by micronutrient fertilization practiced.

Micronutrient application to the soil can occur at any time during the year; however maximum affect has been observed when micronutrient fertilizer is applied in the late summer/early fall or early spring in advance of seasonal plant growth. In western landscapes occupied by invasive weeds, winters are typically cold with snow and frozen ground. Maximum plant growth typically occurs in the spring (April-June when snow melts, ground thaws, soil temperatures warm and spring rains occur). The effect of soil micronutrient application during this period may not be observed for one year as plant growth occurs due to existing soil nutrients rather than the added soil nutrients (unless fertilizer is applied early in the spring and/or unless significant rainfall occurs). Invasive plant species appear most sensitive to elevated micronutrient levels when the plants are young. It should be noted that the effect on invasive plants from micronutrient additions to soil are dissimilar from organic chemical based herbicides that kill plants over a period of days to weeks and are generally applied to the growing leaf tissue. This invention requires sufficient time for the fertilizer to be applied to the soil, become dissolved by rainfall or snowmelt and to change the chemistry of the soil solution such that germinating seed or young plants imbibe the applied trace element solution. Changes to the plant community are best observed over long-periods of time (months-years) compared to conventional organic herbicide applications that take affect over short periods of time. It is unclear whether mature, perennial invasive weeds can be controlled using this method. However, data shows that emergent and young invasive plants (annual or perennial) are readily controlled. This invention also should be thought of in terms of greatly reducing the prevalence of weeds by changing the soil chemistry, but not eliminating all weeds. This is an ecological approach to restoring desirable plant communities and their soil quality. This approach to weed control is fundamentally different than the current practice which focuses solely on the plant and invasive species control as a one component system. This invention changes the soil chemistry to change the plant community as a two component system, each dependent on the other.

The present invention provides a method for preparation of a phytotoxic soil condition to invasive plant species through the application of micronutrients. The formulations of the invention can alternatively be applied as dry powder or as pelletized form offering residual control specifically targeted to seed reserves. According to the present invention, the specific delivery/formulation is less important than being able to control the rate of application relating to the appropriate mass-balance of the micronutrient.

In some embodiments, the present invention involves using a multifunctional surfactant/dispersing agent/thickener/stabilizer when applying the micronutrients to reduce surface tension, improve plant surface adhesion, soil penetration and rewetting and/or to keep all components in a suspension. Alternatively, a separate surfactant/wetting agent and a thickener/stabilizer may be used to accomplish any or all of the above functions. In addition, a multifunctional chelator/dispersant/stabilizer may be included to chelate any of the metal ions present such as the calcium and to trap the excess calcium for later release.

In some embodiments, the present invention involves using a chelating agent when applying the micronutrients. A chelate increases the solubility of the metallic ions and favor the transportation of metallic ions inside the plant. Furthermore, after binding to the metallic ion and later on depositing the metallic ion in the place where the plant requires it, the organic part of the chelate returns to dissolve more ions, which makes the use of the micro nutrients in the soil more prolonged.

In some embodiments, the present invention involves using a surfactant when applying the micronutrients. Use of a surfactant results in a high moisturizing ability and a capacity to decrease the superficial surface tension of the water, which facilitates assimilation of nutrients. On the other hand, due to the ability of the surfactant to form emulsions, the surfactant gives stability to the fertilizer.

The text below offers the example of plant micro-nutrient boron although the same result can be understood by one skilled in the art to also apply to other plant micro-nutrients including, copper, zinc, manganese, iron, chlorine and molybdenum. The expectation is that each invasive or weedy plant species that one is seeking to control or eliminate will have a characteristic sensitivity, tolerance and mortality to each micronutrient. The unique combinations of plant and micronutrient number in the thousands, however this invention has demonstrated that invasive species have lower tolerance and higher sensitivity to micro-nutrients compared to perennial grass species suggesting many possible opportunities for invasive plant control using micronutrient application. Most work performed to date has been performed using boron in the range of 0.5-50 mg/L as a water soluble plant micronutrient. Water soluble micronutrient ranges for copper, zinc, manganese, molybdenum and chlorine for control of invasive plant species are expected to be similarly low, yet the precise targets are expected to be unique to each land area and species targeted. In the instance where existing soil micronutrients are near normal levels prior to treatment to control invasive species target application rates may be lower (e.g. 0.01-0.5 mg/L). The selection of a specific micronutrient and application rate will be made based on species specific sensitivity to each micronutrient and cost for each micronutrient fertilizer.

In an illustrative example of the applicability of the invention to other micronutrients, plant community response to water soluble trace elements has been observed at the Anaconda Smelter Superfund site in Anaconda, Mont. At this site, uncontrolled releases of hazardous substances from the operation of a copper smelter have resulted in sharp gradients in soil concentrations of water soluble copper and zinc. Immediately adjacent to the smelter stack (where the releases originated) soil levels of water soluble copper and zinc are highest and with increasing distance from the smelter stack soil levels of copper and zinc decrease. Along the gradient of water soluble copper and zinc present in the soil, plant community zonation is observed with plants exhibiting tolerance to highly elevated copper and zinc found close to the smelter stack and plants with low tolerance to water soluble copper and zinc found only a great distance from the smelter. Perennial grass species, for example, appear to be tolerant of elevated soil copper and zinc compared to native forbs which are not found near the smelter stack. In the case of dandelions (an invasive plant species), healthy fields of dandelions are found in uncontaminated soils a distance from the smelter. A short distance closer to the smelter, dandelions are very stressed with black leaf spots and reddish leaf margins. Dandelions are not found where moderate to high levels of water soluble copper and zinc are measured in the soil. In contrast the invasive plant species spotted knapweed is found growing in soils with low to high levels of water soluble copper and zinc, suggested differential and elevated tolerance of copper and zinc compared to dandelion.

This invention is also different than the typical herbicidal application of organic chemical formulations to the leaf tissue of growing plants where disruption of plant physiological processes is intended to occur in a short period of time (days-weeks) resulting in death of the plant. Control of weedy plant species through changing the levels of inorganic soil micronutrients (this invention) is intended to restore nutrient levels in disturbed soil typical of the pre-disturbance condition and also restoring the soil's natural ability to recycle plant micronutrients and to preclude weed colonization by maintaining levels of micronutrient fertility harmful to early-successional plant species (weeds) and beneficial to later successional desirable plant species. Disruption of growing plant physiology through application on live plant tissue is not intended. The subject invention is also more likely to have effect over longer periods of time (months-years) as plant micronutrients are made available to plants through root uptake rather than foliar uptake. If foliar micronutrient uptake occurs during application of liquid micronutrient formulation, some measure of invasive species control may occur, yet this is ancillary to the main treatment effect caused by seed or root uptake from the soil. Additionally, herbicidal application of organic chemicals is often an annual process as new plants grow from seed. In the subject invention, the phytotoxic control of weeds by micronutrient application is a one-time application intent on restoring soil health, plant community composition and long-term control of weeds through natural micronutrient cycling. Subsequent micronutrient applications may be required if target soil levels are not attained during a first application due to landscape factors, climate, grazing, fire or related land management activities. Multiple applications of micronutrients are not prohibited by this invention.

The present invention also exploits the life cycle of weedy plant species that rely on prolific seed production and dispersion mechanisms to colonize disturbed and nutrient-depleted sites. In particular, annual weedy plant species must grow from seed to maturity every year to perpetuate the plant's life cycle. By creating phytotoxic soil conditions through micronutrient application (this invention) in the uppermost soil layers (~1 inch depth) weed seeds and seedlings are killed during or immediately following germination therein preventing the plant from growing to maturity and producing seed to sustain subsequent generation of plants. Existing desirable perennial plant species are unharmed due to deeper roots which are not exposed to phytotoxic surficial micronutrient levels. Over a period of months or years the surface applied micronutrients will reach roots in the deeper soil at diluted concentrations which are expected to have a beneficial fertilization affect due to prior nutrient depletion caused by land disturbance. Many disturbed sites are both water limited due to climate and nutrient limited due to soil depletion. The resulting ecological lift is caused by the combined effect of enhancing existing desirable vegetation and diminishing the frequency and extent of weedy plants.

In the embodiment of creating a phytotoxic boron solution, having a boron concentration ranging from 0.01-50 milligrams (mg) or, alternatively, 0.5-50 milligrams (mg) soluble boron per liter (L) is created by dissolving boric acid, sodium borate, sodium tetraborate, or disodium tetraborate, or other soluble sources of boron, in water or alternative liquid to create a boron-containing solution.

Thus, in some embodiments of the present invention, boron or other micronutrients are applied to a locus to achieve a soluble boron soil concentration of about: 0.01 mg/L, 0.02 mg/L, 0.03 mg/L, 0.04 mg/L, 0.05 mg/L, 0.06 mg/L, 0.07 mg/L, 0.08 mg/L, 0.09 mg/L, 0.10 mg/L, 0.15 mg/L, 0.20 mg/L, 0.25 mg/L, 0.30 mg/L, 0.35 mg/L, 0.40 mg/L, 0.45 mg/L, 0.50 mg/L, 0.55 mg/L, 0.60 mg/L, 0.65 mg/L, 0.70 mg/L, 0.75 mg/L, 0.80 mg/L, 0.85 mg/L, 0.90 mg/L, 0.95 mg/L, 1.00 mg/L, 1.50 mg/L, 2.00 mg/L, 2.50 mg/L, 3.00 mg/L, 3.50 mg/L, 4.00 mg/L, 4.50 mg/L, 5.00 mg/L, 5.50 mg/L, 6.00 mg/L, 6.50 mg/L, 7.00 mg/L, 7.50 mg/L, 8.00 mg/L, 8.50 mg/L, 9.00 mg/L, 9.50 mg/L, 10.00 mg/L, 11.00 mg/L, 12.00 mg/L, 13.00 mg/L, 14.00 mg/L, 15.00 mg/L, 16.00 mg/L, 17.00 mg/L, 18.00 mg/L, 19.00 mg/L, 20.00 mg/L, 21.00 mg/L, 22.00 mg/L, 23.00 mg/L, 24.00 mg/L, 25.00 mg/L, 26.00 mg/L, 27.00 mg/L, 28.00 mg/L, 29.00 mg/L, 30.00 mg/L, 31.00 mg/L, 32.00 mg/L, 33.00 mg/L, 34.00 mg/L, 35.00 mg/L, 36.00 mg/L, 37.00 mg/L, 38.00 mg/L, 39.00 mg/L, 40.00 mg/L, 41.00 mg/L, 42.00 mg/L, 43.00 mg/L, 44.00 mg/L, 45.00 mg/L, 46.00 mg/L, 47.00 mg/L, 48.00 mg/L, 49.00 mg/L, and 50.00 milligrams per liter of soil.

In other embodiments of the present invention, boron or other micronutrients are applied to a locus to achieve soluble boron soil concentration ranges as follows (including any/all concentrations between these ranges): 0.01-0.02 mg/L, 0.02-0.03 mg/L, 0.03-0.04 mg/L, 0.04-0.05 mg/L, 0.05-0.06 mg/L, 0.06-0.07 mg/L, 0.07-0.08 mg/L, 0.08-0.09 mg/L, 0.09-0.10 mg/L, 0.10-0.15 mg/L, 0.15-0.20 mg/L, 0.20-0.25 mg/L, 0.25-0.30 mg/L, 0.30-0.35 mg/L, 0.35-0.40 mg/L, 0.40-0.45 mg/L, 0.45-0.50 mg/L, 0.50-0.55 mg/L, 0.55-0.60 mg/L, 0.60-0.65 mg/L, 0.65-0.70 mg/L, 0.70-0.75 mg/L, 0.75-0.80 mg/L, 0.80-0.85 mg/L, 0.85-0.90 mg/L, 0.90-0.95 mg/L, 0.95-1.00 mg/L, 1.00-1.50 mg/L, 1.50-2.00 mg/L, 2.00-2.50 mg/L, 2.50-3.00 mg/L, 3.00-3.50 mg/L, 3.50-4.00 mg/L, 4.00-4.50 mg/L, 4.50-5.00 mg/L, 5.00-5.50 mg/L, 5.50-6.00 mg/L, 6.00-6.50 mg/L, 6.50-7.0 mg/L, 7.00-7.50 mg/L, 7.50-8.0 mg/L, 8.00-8.50 mg/L, 8.50-9.0 mg/L, 9.00-9.50 mg/L, 9.50-10.00 mg/L, 10.00-10.50 mg/L, 10.50-11.00 mg/L, 11.00-11.50 mg/L, 11.50-12.00 mg/L, 12.00-13.00 mg/L, 13.00-14.00 mg/L, 14.00-15.00 mg/L, 15.00-16.00 mg/L, 16.00-17.00 mg/L, 17.00-18.00 mg/L, 18.00-19.00 mg/L, 19.00-20.00 mg/L, 20.00-21.00 mg/L, 21.00-22.00 mg/L, 22.00-23.00 mg/L, 23.00-24.00 mg/L, 24.00-25.00 mg/L, 25.00-26.00 mg/L, 26.00-27.00 mg/L, 27.00-28.00 mg/L, 28.00-29.00 mg/L, 29.00-30.00 mg/L, 30.00-

31.00 mg/L, 31.00-32.00 mg/L, 32.00-33.00 mg/L, 33.00-34.00 mg/L, 34.00-35.00 mg/L, 35.00-36.00 mg/L, 36.00-37.00 mg/L, 37.00-38.00 mg/L, 38.00-39.00 mg/L, 39.00-40.00 mg/L, 40.00-41.00 mg/L, 41.00-42.00 mg/L, 42.00-43.00 mg/L, 43.00-44.00 mg/L, 44.00-45.00 mg/L, 45.00-46.00 mg/L, 46.00-47.00 mg/L, 47.00-48.00 mg/L, 48.00-49.00 mg/L, and 49.00-50.00 milligrams per liter of soil.

In one embodiment, the 5 mg B/L concentration is achieved by dissolving 29.4 mg boric acid in 1000 milliliters of water. In another embodiment, the 20 mg B/L concentration is achieved by dissolving 117.6 mg boric acid in 1000 milliliters of water. In each case, the solution is thoroughly mixed to assure complete dissolution of the boron. The solution is then applied as an aerial spray to the target area. The solution is applied to the surface of soil containing invasive species seed, directly to weed seed, or to senesced or live, seed-bearing weed plants at a rate of 2-200 milliliters per square meter. A target area may be any plant community where invasive species are present, e.g. urban land, rangeland, forestland, roadside, brownfield, or disturbed land.

As used herein, the phrase "urban land" refers to an area having the characteristics of a city or otherwise developed for human habitation, with intense development and a wide range of public facilities and services.

As used herein, the term "rangeland" refers to an expanse of land suitable for livestock or wildlife to wander and graze on.

As used herein, the term "forestland" refers to a section of land covered with forest or set aside for the cultivation of forests or as wildland without silvicultural intent.

As used herein, the term "brownfield" refers to a piece of industrial or commercial property that is abandoned or underused and often environmentally contaminated, especially one considered as a potential site for redevelopment.

As used herein, the phrase "disturbed land" refers to land that has been physically disturbed by resource operations (e.g., from mining, logging or construction) that cannot be used for other purposes (e.g., for agriculture or home sites). Disturbed land may be caused by, but not limited to, grazing by wildlife and domestic animals, fire, road construction, climate change, flooding, landslide, erosion, invasive species colonization, tillage for agriculture, urbanization, pipeline or utility installation, dam building (or removal), and the like.

In some embodiments of the present invention, the target area does not include land under intensive agronomical or horticultural production. For example, in some embodiments of the present invention, the target area does not include land being used to grow row crops, such as is used for large-scale growing of soybeans, maize/corn, cotton, dry peas and the like. In other examples, in some embodiments of the present invention, the target area does not include land being used to grow truck crops (i.e., large-scale vegetable crops), such as is used for large-scale growing of watermelons, fresh peas, peppers, cucumbers, tomatoes, onions and the like. In still other examples, in some embodiments for the present invention, the target area does not include land being used to grow large-scale production of flowers, such as is used for large-scale growing of tulips, daffodils, chrysanthemums and the like.

When applied as a dry, spreadable powder, the specific source of boron is crystalline, powdered boric acid, or other boron-containing compounds and/or fertilizers. In an embodiment of dry boron application in dry flowable form, 1.98 g boric acid per square meter is applied to the target area. Other excipients can be added to the formulation to enhance or ensure the composition remains flowable to the desired consistency. The dry flowable form is applied to the surface of soil containing weed seed, directly to weed seed, or to senesced or live, seed-bearing weed plants.

Applying a boron-containing formulation to weed seeds, weed seedlings, and/or weed plants functions by disrupting the target species cell physiology when moisture containing boron is imbibed by the seed or seedling from the soil. While control of invasive plant species is the outcome of the invention, the applications of micronutrients are intended to change the soil chemistry. The soil is the host of the micronutrients delivered to the invasive plant species. In each application embodiment, whether liquid or dry, the applied boron is made plant-available either through dissolution by rainfall, snowmelt or other environmental conditions, or plant uptake of the liquid application, and is therefore plant-available regardless of the form of application. The actual mechanism of boron involvement in plant physiology remains somewhat unclear. There is a very narrow window between the levels of boron required by and toxic to plants. The subject invention discloses the specific, narrow window of concentrations of boron toxic to invasive plant species, thereby allowing control by application of boron concentrations in excess of invasive plant species toxic limits, yet below levels toxic to desirable species.

Another embodiment of the invention entails measuring the amount of plant-available boron in the soil in the target area and adding supplemental boron to achieve an effective level harmful to invasive plant species, but not harmful to desirable vegetation (also referred to as the Induced Phytotoxicity Threshold or IPT). Under this embodiment the naturally occurring soil boron level is measured therein establishing a baseline boron concentration. This method is made possible by laboratory, greenhouse and field testing of common plant species and development of unique characteristic dose-response curves identifying plant growth characteristics resulting from varying the water soluble boron concentrations across the range of 0.5 to 50 mg/L. The novel finding that facilitates the invention is the sensitivity of invasive plants species to low levels of water soluble soil boron compared to desirable plant species found on rangeland or other environments.

Each of the embodiments of the present invention as described herein for preparation and application of boron are similarly applicable to formulations containing the other micronutrients useful for this invention. Such formulations containing the other micronutrients, or combinations thereof, may be similarly prepared and applied to a target area, depending on the invasive species that is to be controlled or eradicated and the IPT for that species, micronutrient and target area soil conditions or preexisting micronutrient levels.

Boron toxicity to invasive plant species appears to cause significant changes in the physiology and activity of numerous enzymes in seed and seedling development, and consequently plant metabolism during the life cycle of the plant. Three main candidates for boron toxicity involve the ability of boron to bind compounds with two hydroxyl groups in the cis-configuration: (a) alteration of cell wall structure; (b) metabolic disruption by binding to the ribose moieties of molecules such as adenosine triphosphate (ATP), nicotimamide adenine dinucleotide; and (c) disruption of cell division and development by binding to ribose, either as a free sugar or within RNA. However, the only defined physiological role of boron in plants is as a cross-linking molecule involving reversible covalent bonds with cis-diols on either side of borate. Because boronic acids cannot cross-link two molecules, the addition of boronic acids causes the disruption of cytoplasmic strands and cell-to-cell wall detachment. Boronic acids appear to specifically disrupt or prevent borate-dependent cross-links important for the structural integrity of the cell, including the organization of transvacuolar cytoplasmic strands. Boron likely plays a structural role in the plant cytoskeleton.

Many variations of the invention will occur to those skilled in the art. Some variations include plant micronutrients in addition to or in place of boron. Known plant micronutrients include boron, copper, zinc, manganese, iron, chlorine and molybdenum. Other variations call for variations and ranges of the concentrations of each element being applied, and the compound source for the micronutrient. See, e.g., Table 1 supra. Other variations include application of combinations of more than one plant micronutrient. Other variations include application of micronutrients with macronutrients nitrogen (N), phosphorous (P) or potassium (K). Additional variations include the targeted invasive plant species subject to control or eradication. Additional variations include the type of site or landscape the methods and compositions of this invention may be applied to. There are many different techniques which may be used to apply or distribute a specific form of the compounds (whether liquid or dry). The application rate can be adjusted across a range from low to high concentration to reduce, control, and eliminate/eradicate a particular invasive plant species or species. The application rate can be adjusted and applied to protect against future invasion by invasive species. The application rate can also be applied at such levels to cause a phytotoxic condition for all plants resulting in bare ground. All such variations are intended to be within the scope and spirit of the invention.

Although some embodiments are shown to include certain features or steps, the applicant specifically contemplates that any feature or step disclosed herein may be used together or in combination with any other feature or step in any embodiment of the invention. It is also contemplated that any feature or step may be specifically excluded from any embodiment of the invention.

The utility of this invention is multi-fold and includes but is not limited to the following uses:

a) The invention is useful for control or eradication of invasive plant species currently occupying more than 100 million acres in the U.S.;
b) The invention comprises non-synthetic, non-organic naturally occurring inorganic earth elements, which are known plant nutrients, non-carcinogenic and non-impairing to soil and water resources at the low concentrations involved in this invention;
c) The invention comprises relatively inexpensive, easily accessible materials, combined with relatively simplified methods of utilization;
d) Boric acid, borate salts or boron (and the other micronutrients of the invention) are neither classified as endocrine disruptors nor are they currently on the list of compounds being screened by the U.S. EPA as part of the Endocrine Disruptor Screening Program (EDSP) for potential in humans;
e) Boric acid and borate salts (and the other micronutrients of the invention) are classified by the U.S. EPA as "not likely to be carcinogenic to humans" under the 2005 carcinogen assessment guidelines;
f) There is no reported risk from occupational exposures studies indicating the carcinogenicity of boric acid, borate salts or boron (and the other micronutrients of the invention);
g) The effectiveness and use of the subject invention is facilitated by the application of relatively small/minute amounts of material required to treat large areas of land;
h) The invention is specifically selective to weedy plant species, allowing the invention to be used on land parcels of mixed plant communities without significant adverse impact on desired plant species;
i) The invention allows for application of low concentrations of micronutrient-containing compositions to plants, seeds, seedlings or soil which results in phytotoxic responses of weedy species while minimizing impact to existing desirable native plant species.

The methods of the present invention use micro-nutrients required in small amounts by most vascular plants, as an herbicide or chemical agent against invasive plant species. The formulations of the invention effectively cause the death of live plant, seedlings, or seeds of invasive plant species, when the soluble trace element comes in contact with germinating seed or are taken up by the roots of live plants. Similarly, the formulations of the invention effectively cause the death of seedlings of invasive plant species, when the trace element comes in contact with the emerging seedlings. The findings of the inventor are unexpected and surprising. One skilled in the art may expect that based on scientific literature and accepted agronomic practices that the addition of micro-nutrients to soil for uptake by plants would enhance plant performance of all species, rather than cause selective death to seed, emerging seedlings or live plants. Also surprising, the application of relatively low concentrations of micro nutrient-containing formulations which are phytotoxic to invasive species do not result in harm to desirable native species, or at least are less harmful over a spectrum of desirable native species. The invention provides a significant new tool and method for land managers to effectively control or eradicate invasive species over a wide variety of acreages and may be modified to suit site conditions, including specific plant communities. The low rates of application are also manifested in low unit cost per land area treated.

Although scientific literature reports instances of trace element toxicity to vascular plants, these instances of toxicity typically have occurred in response to unusually high concentrations of trace elements. The inventor is not aware of any prior art wherein trace elements, in minute quantities, are used for the specific purpose of plant, seed or seedling death of unique species, i.e., constituting 'weed control'. Of the sixteen chemical elements known to be important to a plant's growth and survival, thirteen come from the soil, are dissolved in water and absorbed through a plant's roots. In some instances, there are not always enough of these nutrients in the soil for a plant to grow healthy. In other instances, some combinations and concentrations of these nutrients, particularly the micronutrients, can be detrimental or toxic to some plants. Micronutrients, those elements essential for plant growth and which are needed in only very small (micro) quantities, are boron (B), copper (Cu), iron (Fe), chlorine (Cl), manganese (Mn), molybdenum (Mo) and zinc (Zn). These micronutrients play critical roles in carbohydrate transport, metabolic regulation, osmosis and ionic balance, enzyme and chlorophyll synthesis and function, internal chemical transformations, and cell reproduction/division.

Extensive research has documented that plants are often sensitive to relatively minute concentrations or exposures to unique synthetic compounds or combinations of naturally occurring elements, including micro-nutrients. For example, glyphosate (aka ROUNDUP®, a synthetic Monsanto product) is effective at causing photosynthetic disruption in chlorophyllitic plants at an application rate of as little as 0.75 pounds active ingredient per acre, which equates to only approximately 8 mg/square foot of application, equivalent to approximately 14 ppm application rate. The American Phytopathological Society (APS) reported that micronutrients are generally toxic when present in high amounts, although 'high concentrations' are not clearly defined, and little toxicity have been reported at exceptionally low micronutrient concentrations. This occurrence is known as micronutrient toxicity syndrome (MTS). As an example, Jong et al. (1996) reported micro-nutrient toxicity in French marigold induced from boron, copper, iron, manganese, molybdenum, and zinc at concentrations of 0.5, 4, 2, 1 and 5 mg/L, respectively. In addition, plants can vary considerably from species to species in their susceptibility to nutrient toxicities. For example, Lee and others (1996) reported inducing seed geranium (*Pelargonium×hortorum*) micronutrient toxicity symptoms by applying nutrient solutions containing 0.5 mg/L B, Cu, or Zn, or as little as 0.25 mg/L Mo, in combination with nitrogen, phosphorus, and potassium. Micronutrient toxicity has also been reported for Begonia, Chrysanthemum, Geraniums, Marigolds, Poinsettia, and *Lilium longiflorum* (Hammer et al. 1987; Jong-Myung et al. 1996; Lee et al. 1996; Marousky, 1981).

The toxic effects of excessive application of nutrients to agricultural and horticultural crops are well documented. Even the macronutrient nitrogen can be toxic to plants if applied in excess. Similarly, excessive application of micronutrients can cause phytotoxic effects. However, excessive micronutrient concentrations are rarely found in native soils, with the exception of mineralized areas. In mineral soils, release of micronutrients is usually quite slow. Much of the available soil micronutrients are held rather tightly by soil organic material and thus toxicity to plants is not a frequent occurrence under 'field' conditions. For the majority of landscape plants micro-nutrient concentrations in the saturated soil paste extract between 0.15-0.5 parts per million are desired. Depending on plant sensitivity, some of these elements can be toxic at soil test concentrations above one part per million. Nutrient toxicity does not often occur in most arable soils. Such toxicity exerts different effects on very diverse processes in vascular plants, such as altered metabolism, reduced root cell division, lower leaf chlorophyll contents and photosynthetic rates, and decreased lignin and suberin levels, among others (Nable et. al. 1997; Reid 2007b). Accordingly, reduced growth of shoots and roots is typical of plants exposed to high micro-nutrient levels (Nable et al. 1990). Referring to Keren and Bingham (1985), safe concentrations of micro-nutrients in irrigation water range from 0.3 mg/L for sensitive plants [i.e. avocado (*Persea americana*), apple (*Malus domestica*) and bean (*Phaseolus vulgaris*)], 1-2 mg/L for semi tolerant plants [oat (*Avena sativa*), maize (*Zea mays*), potato (*Solanum tuberosum*)], and 2-4 mg/L for tolerant plants [i.e. carrot (*Daucus carota*), alfalfa (*Medicago sativa*) and sugar beet (*Beta vulgaris*)].

Sensitivity of cheatgrass (*Bromus tectorum*), dandelion (*Taraxacum officinale*), spotted knapweed (*Centaurea maculosa*) and other weedy species to micro-nutrients has not been reported in the scientific literature. The literature identifies boron, copper, zinc, manganese and molybdenum as potential plant toxins at 'elevated' concentrations unique to each species. The literature does not suggest a method for selectively controlling undesirable plant species (i.e. weeds) by application of micro-nutrients above the phytotoxic threshold for that species.

Current techniques used for invasive plant species control are largely limited in their effectiveness as they are indiscriminately harmful to all existing vegetation to which they are applied (i.e. glyphosate), or are harmful to non-target species to which they are applied of the same life form as the invasive species (i.e. collateral damage to forbs with 2,4-D application). The fertilizer and weed control industries are multi-billion dollar entities. Invasive plant management is a pervasive problem on as much as 100 million acres in the U.S., with only marginally effective control methods. The methods of the subject invention offer a cost-effective means to address invasive plant invasion and the associated economic losses due to diminished land productivity, yet without collateral damage to the environment.

EXAMPLES

The invention will now be illustrated in greater detail by reference to the specific embodiments described in the following examples. The examples are intended to be purely illustrative of the invention and are not intended to limit its scope in any way.

Example 1

Field trials were established in existing perennial grass communities near Belgrade, Mont., with high levels of cheatgrass and dandelion invasion into existing perennial grasses to examine use of boron (elemental symbol: B) fertilization for weed control. Minute amounts of boron, in doses as low as 5 mg B/L (soluble) or 2-3 lbs B (dry) active ingredient per acre, were applied to the plots.

Subsequent observations in following growing seasons confirmed the near-total absence of either emerging or mature cheatgrass plants in these plots, with a return to perennial grass dominated community over a 5 year period using a single application of boron fertilizer. Over the same period of time dandelion cover decreased from a mean of 59% to 15%, and cheatgrass cover decreased from a mean of 47% to 1%, while perennial grass cover increased from 42% to 71%.

FIG. 1A presents the mean dandelion, cheatgrass and perennial grass cover over 5 growing seasons to applications of dry formulations of boron fertilizer.

Figure 1B:
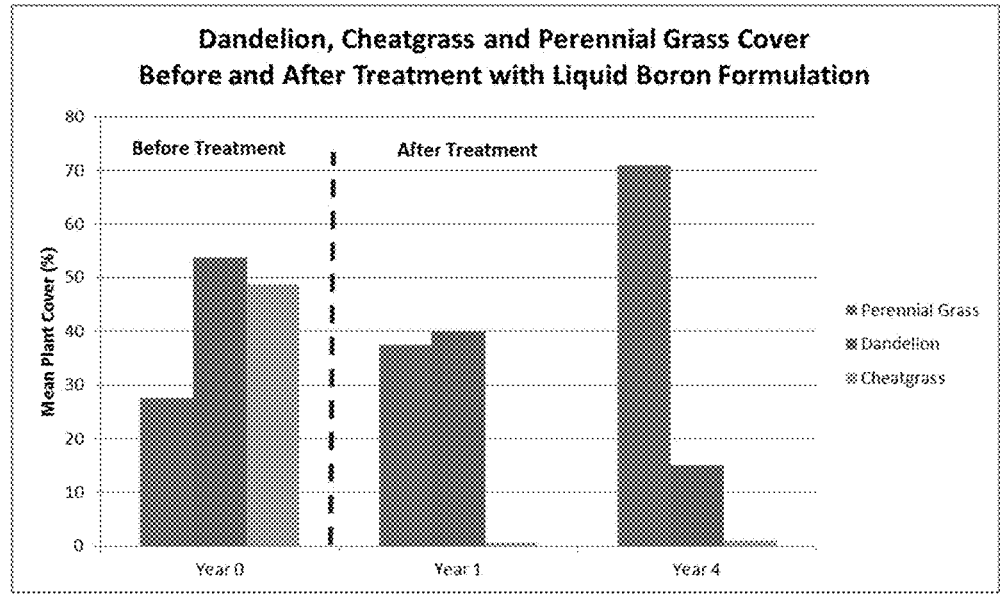
FIG. 1B illustrates the percent mean plant cover of dandelion (*Taraxacum officinale*), cheatgrass (*Bromus tectorum*) and perennial grass (several species) over a 5 year time period following application of liquid formulations of varying boron concentrations at a field site in Belgrade, Mont.

FIG. 1B presents the mean dandelion, cheatgrass and perennial grass cover over 5 growing seasons to applications of liquid formulations of boron fertilizer.

Example 2

Figure 2B:
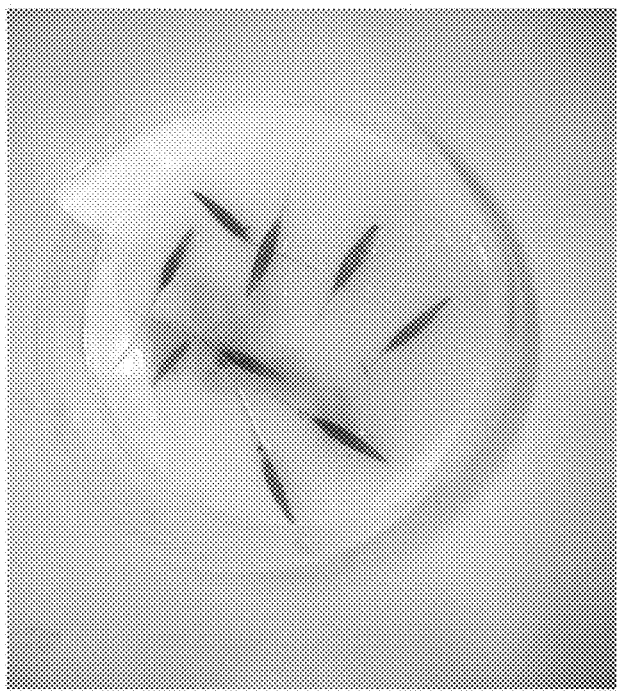
FIG. 2B illustrates zero percent (0%) cheatgrass seed germination 14 days post treatment with boron solution at an effective concentration of 10 mg/L.
Figure 2A:
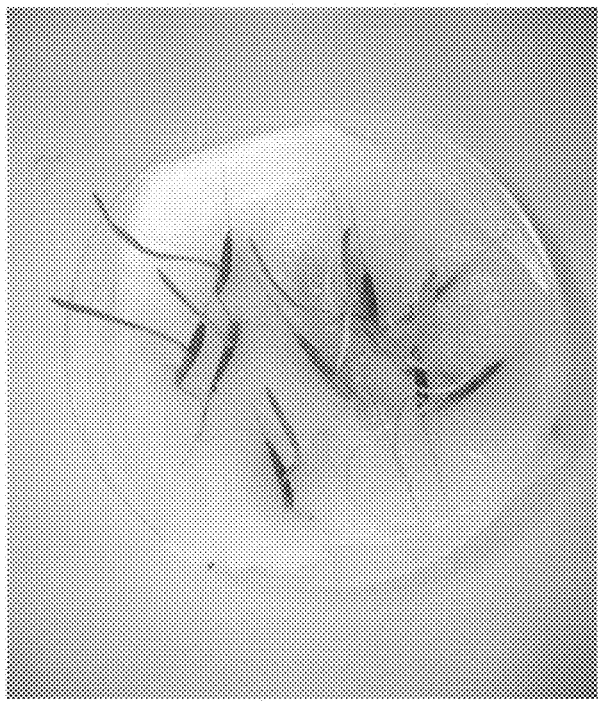
FIG. 2A illustrates one hundred percent (100%) cheatgrass seed germination five days post wetting with distilled water (control treatment).

Greenhouse petri dish experiments were completed to evaluate the effect of minute concentrations of boron on cheatgrass seed germination. Treatment concentrations (in addition to a zero treatment control) ranged from 10 to 50 mg B/L dissolved in distilled water. Control treatments germinated at 100% within 5 days (FIG. 2A), while all of the seed treated with boron exhibited zero percent germination after 14 days (FIG. 2B). A follow-up experiment, essentially repeating the previously described petri dish experiment, with inclusion of a treatment rate as low as 5 mg/L, was completed. It was observed that cheatgrass seeds germinated at the 5 mg/L concentration, with death of the seedlings occurring within 7 days of germination (data not shown).

Example 3

In a greenhouse pot study Kentucky bluegrass, bluebunch wheatgrass, cheatgrass, dandelion and spotted knapweed were grown from seed in potting soil for a period of approximately 26 weeks. Plants were watered with tap water for the first 24 weeks and then 3 times with boron solutions during the final 2 weeks of the study. Boron concentrations used were 5, 10, 25 and 50 mg B/L in addition to a tap water treatment and a commercial plant fertilizer solution.

Figure 3A:
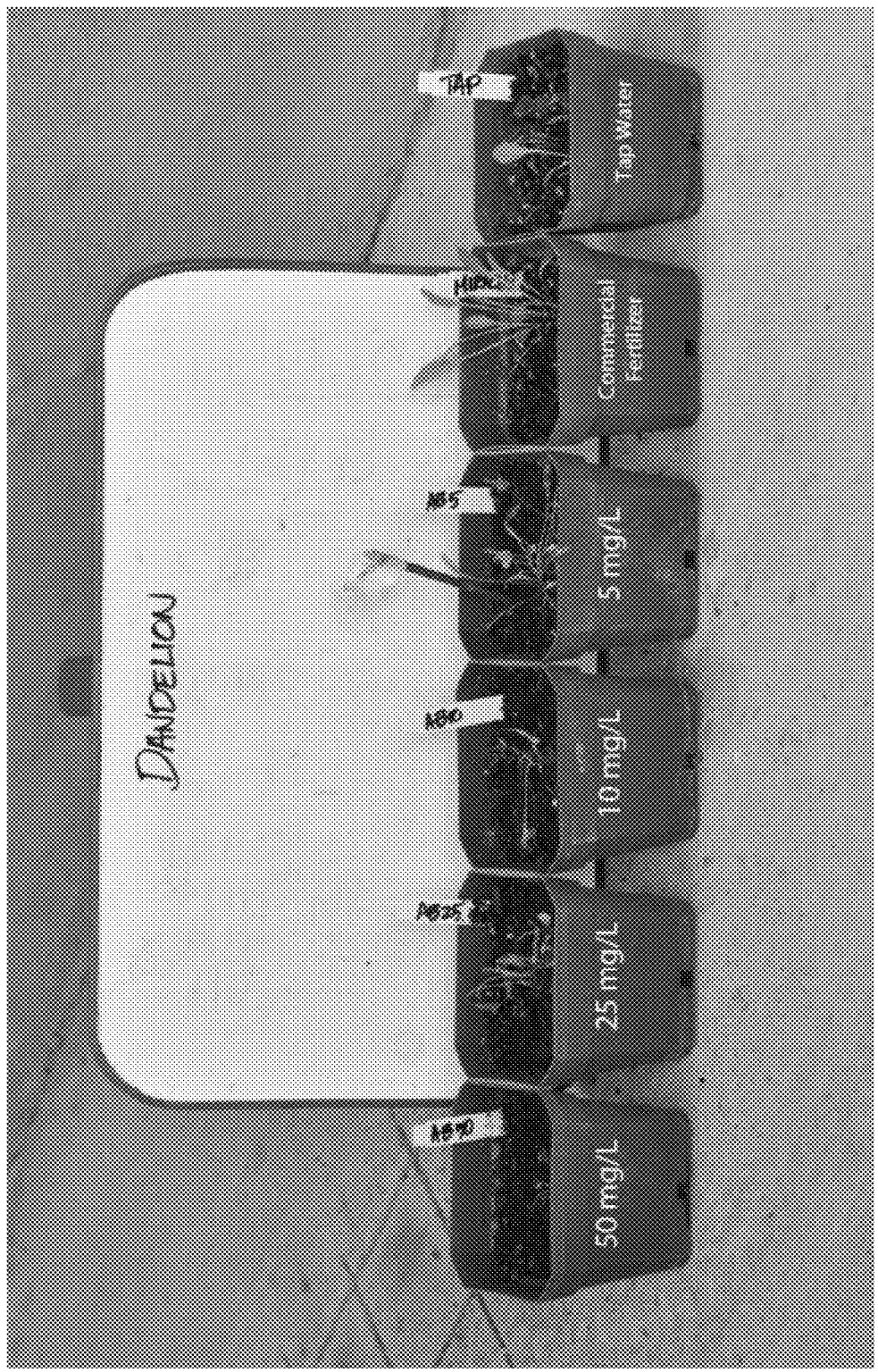
FIG. 3A illustrates the growth of invasive species dandelion (*Taraxacum officinale*) in a small pot study with varying soil boron concentrations of 5, 10, 25 and 50 mg/L compared to plant growth in pots watered with tap water and a commercial fertilizer.
Figure 3B:
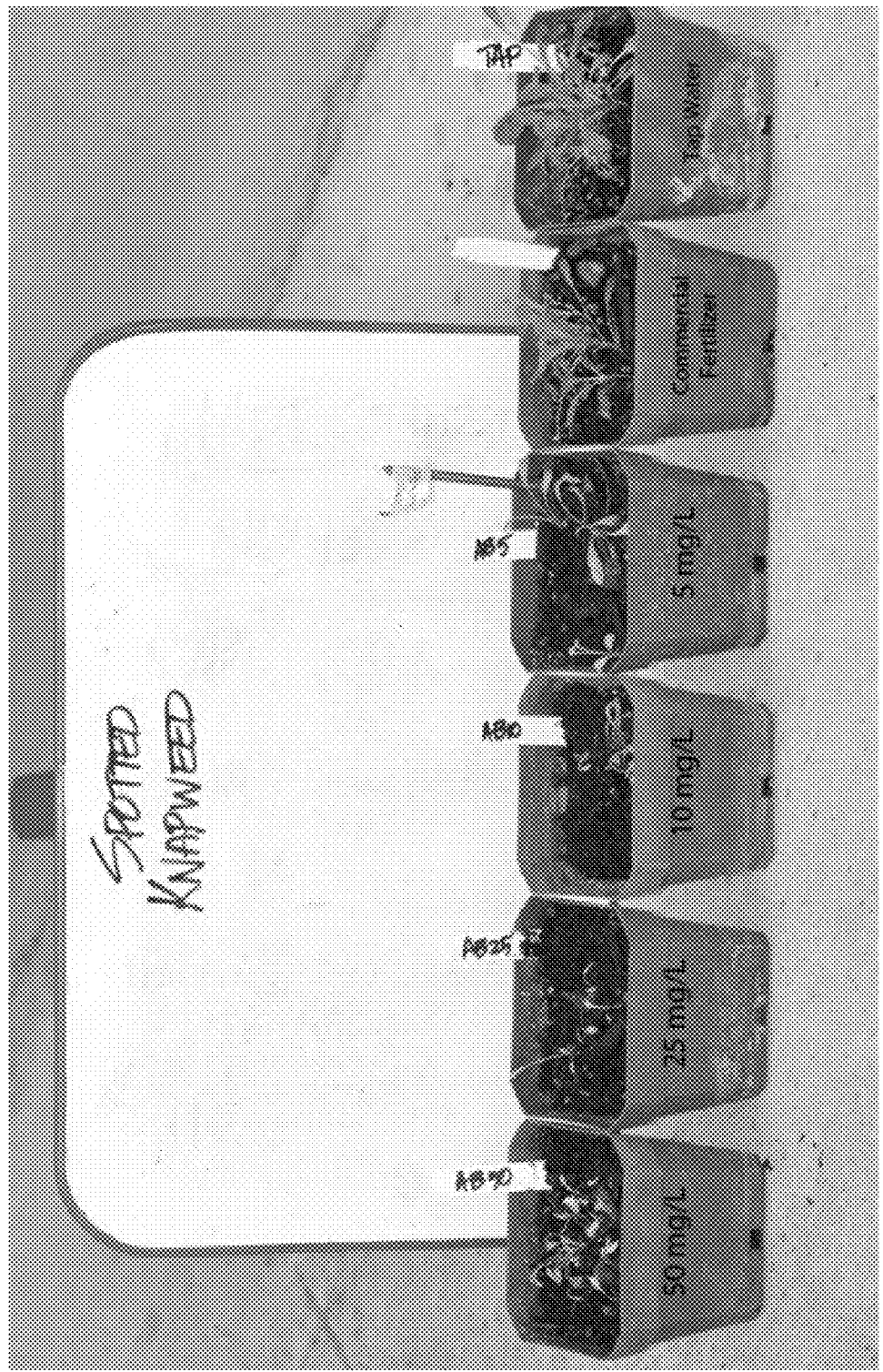
FIG. 3B illustrates the growth of invasive species spotted knapweed (*Centaurea maculosa*) in a small pot study with varying soil boron concentrations of 5, 10, 25 and 50 mg/L compared to plant growth in pots watered with tap water and a commercial fertilizer.

FIG. 3A shows the phytotoxic response to dandelion resulting from watering with boron solutions, while FIG. 3B shows a similar response to spotted knapweed. Both species showed marked phytotoxicity at the lowest boron solution concentration used (5 mg B/L).

Figure 3C:
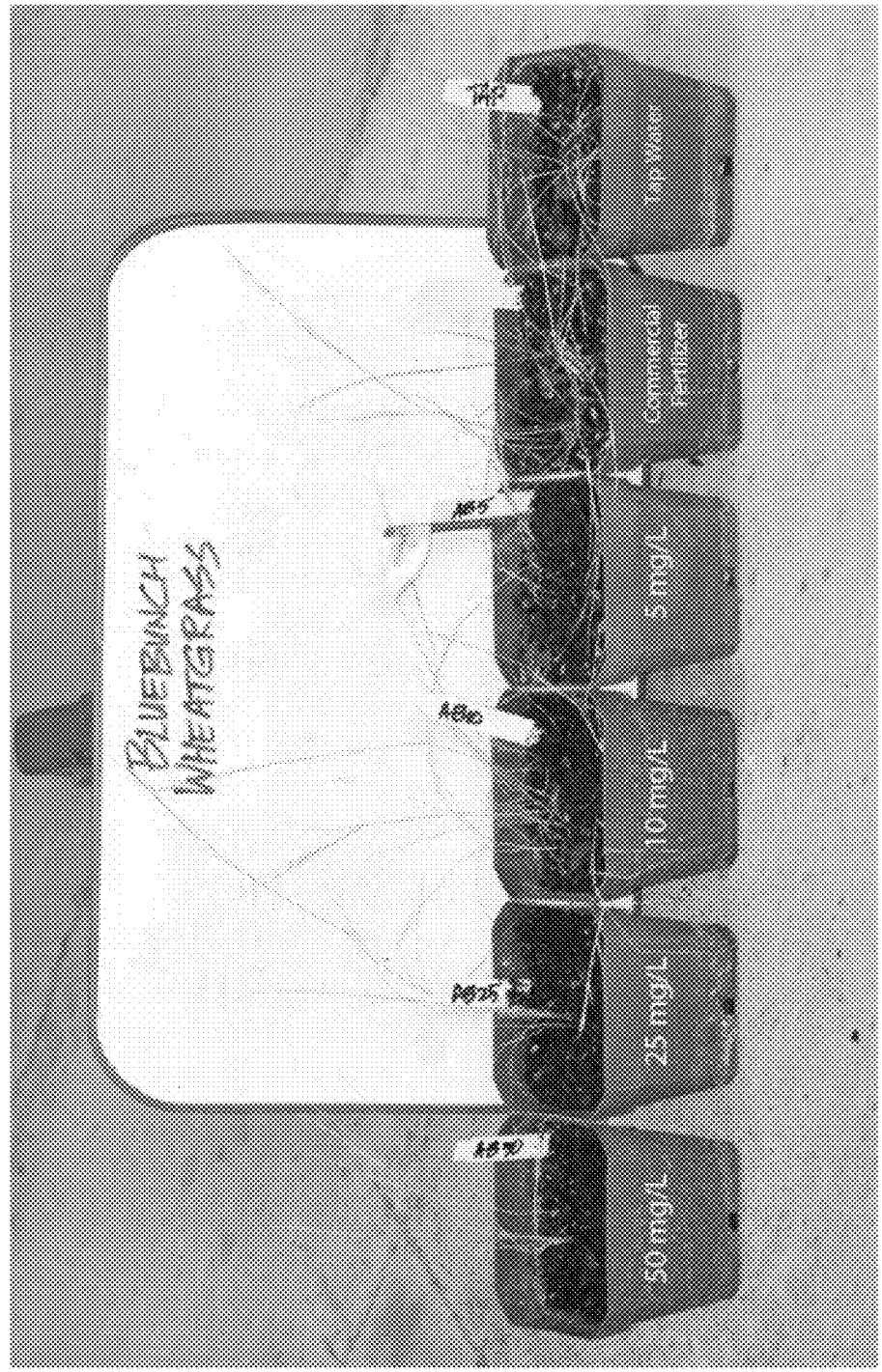
FIG. 3C illustrates the growth of desirable species bluebunch wheatgrass (*Pseudoroegenaria spicata*) in a small pot study with varying soil boron concentrations of 5, 10, 25 and 50 mg/L compared to plant growth in pots watered with tap water and a commercial fertilizer.

FIG. 3C shows the minimal effect to a desirable rangeland grass species (bluebunch wheatgrass) to the same solutions. Bluebunch wheatgrass was able to tolerate concentrations of boron at or above 50 mg B/L.

Figure 3D:
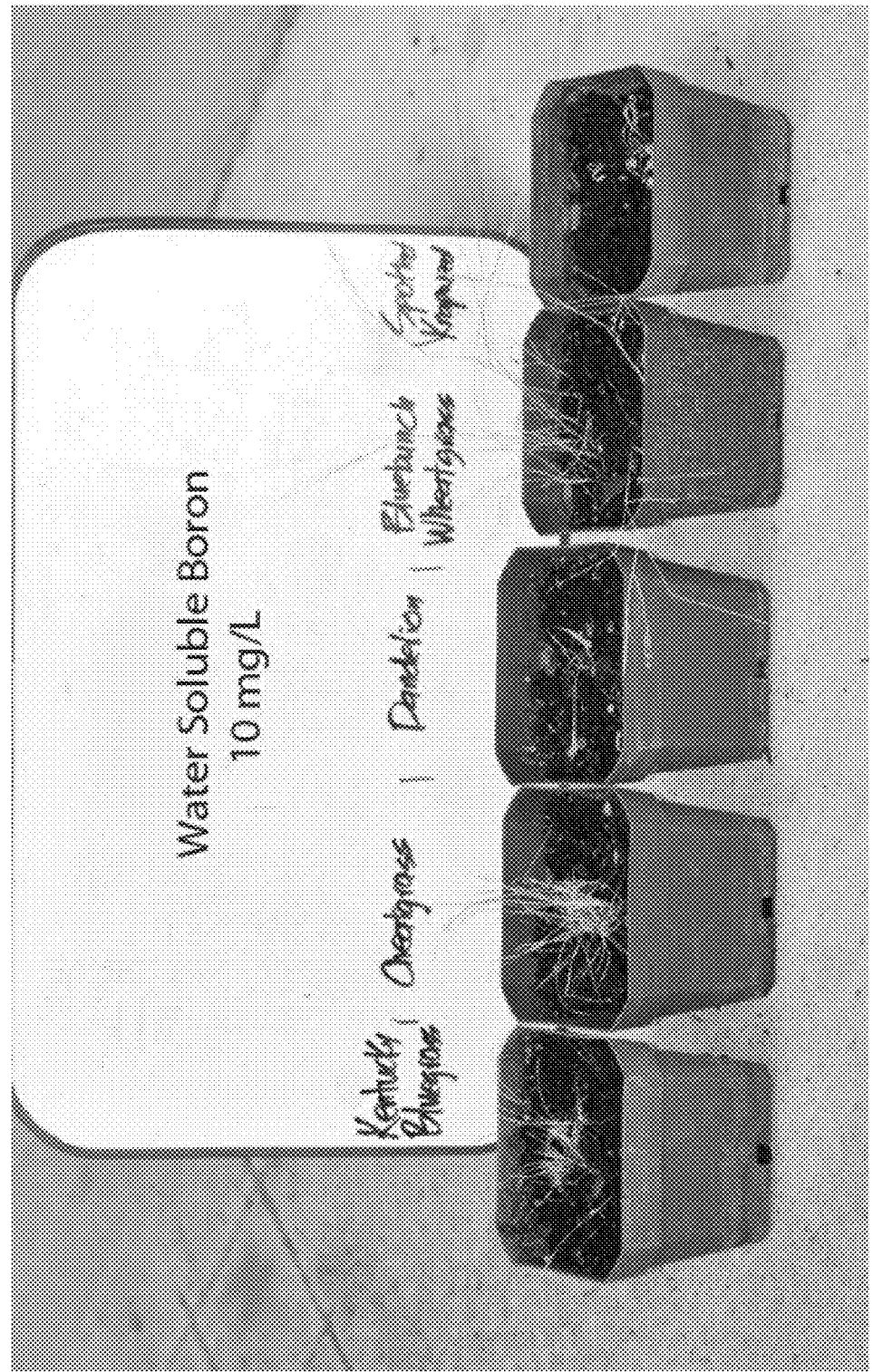
FIG. 3D illustrates the growth of both desirable species bluebunch wheatgrass (*Pseudoroegenaria spicata*), Kentucky bluegrass (*Poa pratensis*) and invasive species dandelion (*Taraxacum officinale*), spotted knapweed (*Centaurea maculosa*) and cheatgrass (*Bromus tectorum*) in a small pot study with a fixed soil boron concentrations of 10 mg/L.

FIG. 3D shows the response of Kentucky bluegrass, cheatgrass, dandelion, bluebunch wheatgrass and spotted knapweed to the 10 mg/L boron solution. Responses varied across species at this concentration.

Example 4

Figure 4:
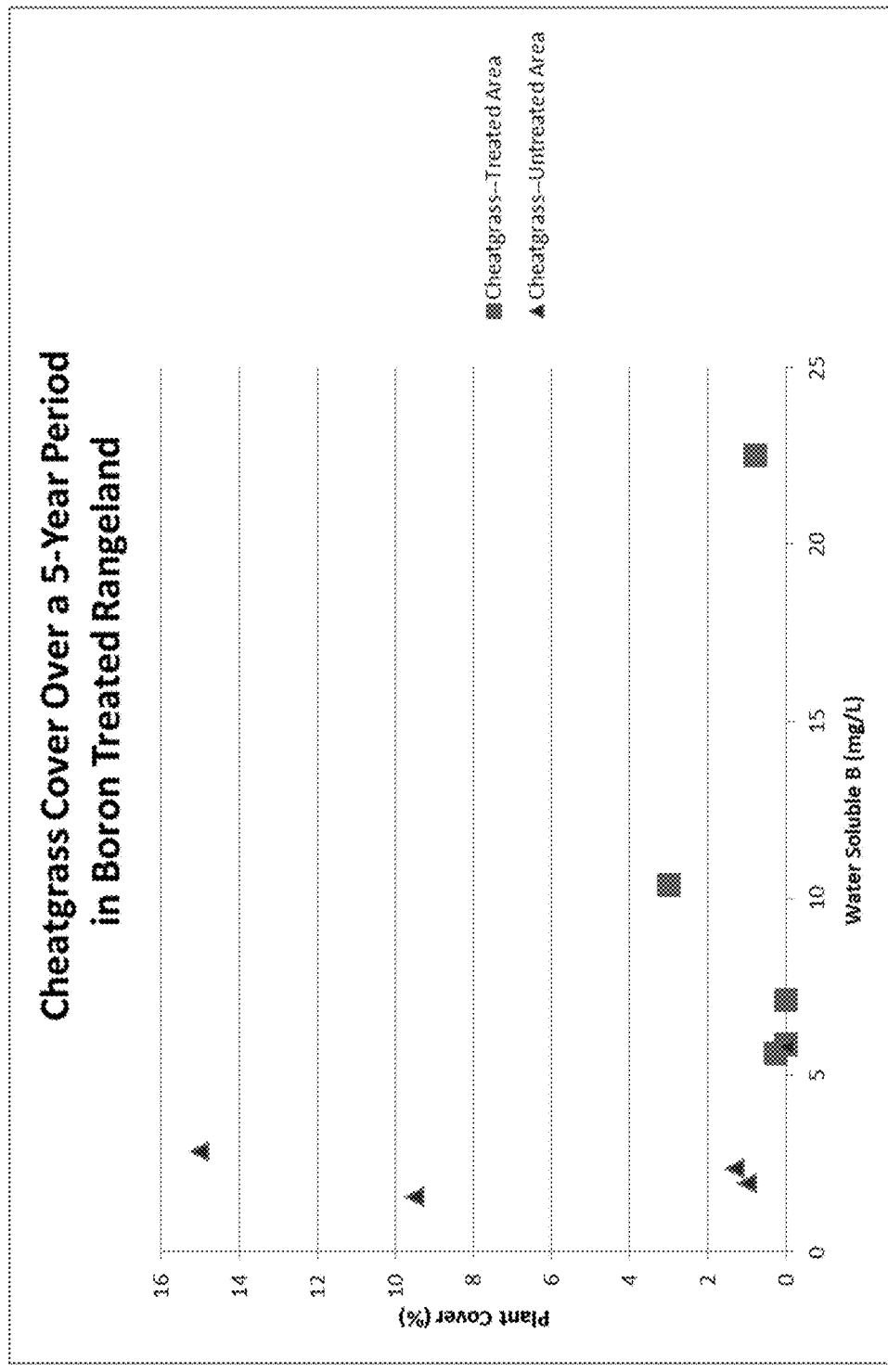
FIG. 4 illustrates rangeland site cheatgrass percent plant cover over a five-year study period in response to water soluble boron concentrations in soil caused by surface boron applications resulting in soil boron concentrations greater than 20 mg/L.

Rangeland site cheatgrass plant cover over a five-year study period in response to water soluble boron concentrations in soil resulting from surface liquid boron applications. Perennial grass densities were observed to increase over time in the treated area, while the adjacent native range site remained weedy with abundant cheatgrass cover (FIG. 4). Soil sampling of the 0-6 inch depth was performed annually to determine the water soluble boron concentrations both in the treated and untreated areas. Transects were used to measure plant cover annually at sites co-located with soil sampling.

Example 5

Figure 5A:
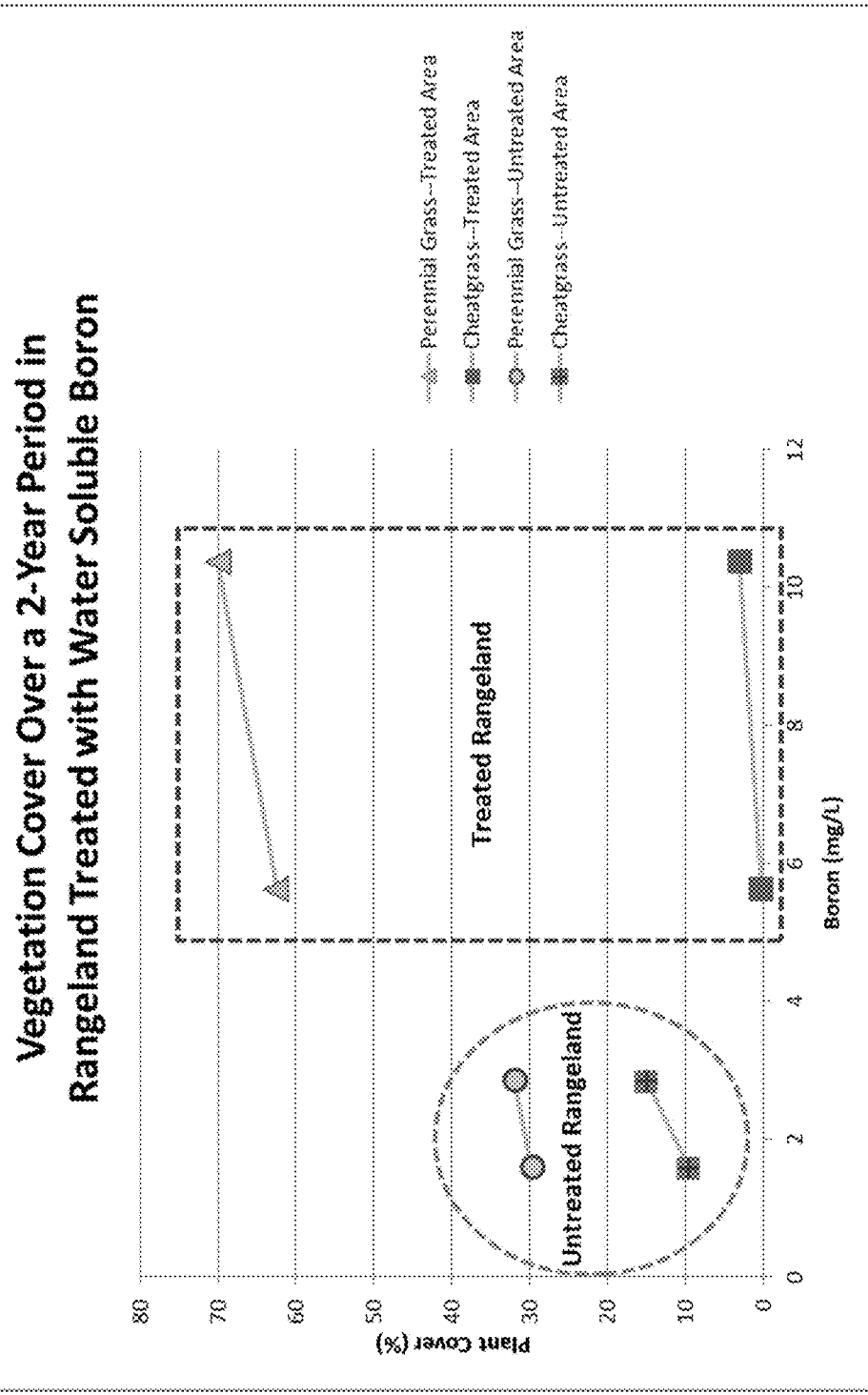
FIG. 5A illustrates rangeland site cheatgrass (*Bromus tectorum*) percent plant cover over a two-year study period in response to water soluble boron concentrations in soil resulting from liquid surface boron application.
Figure 5B:
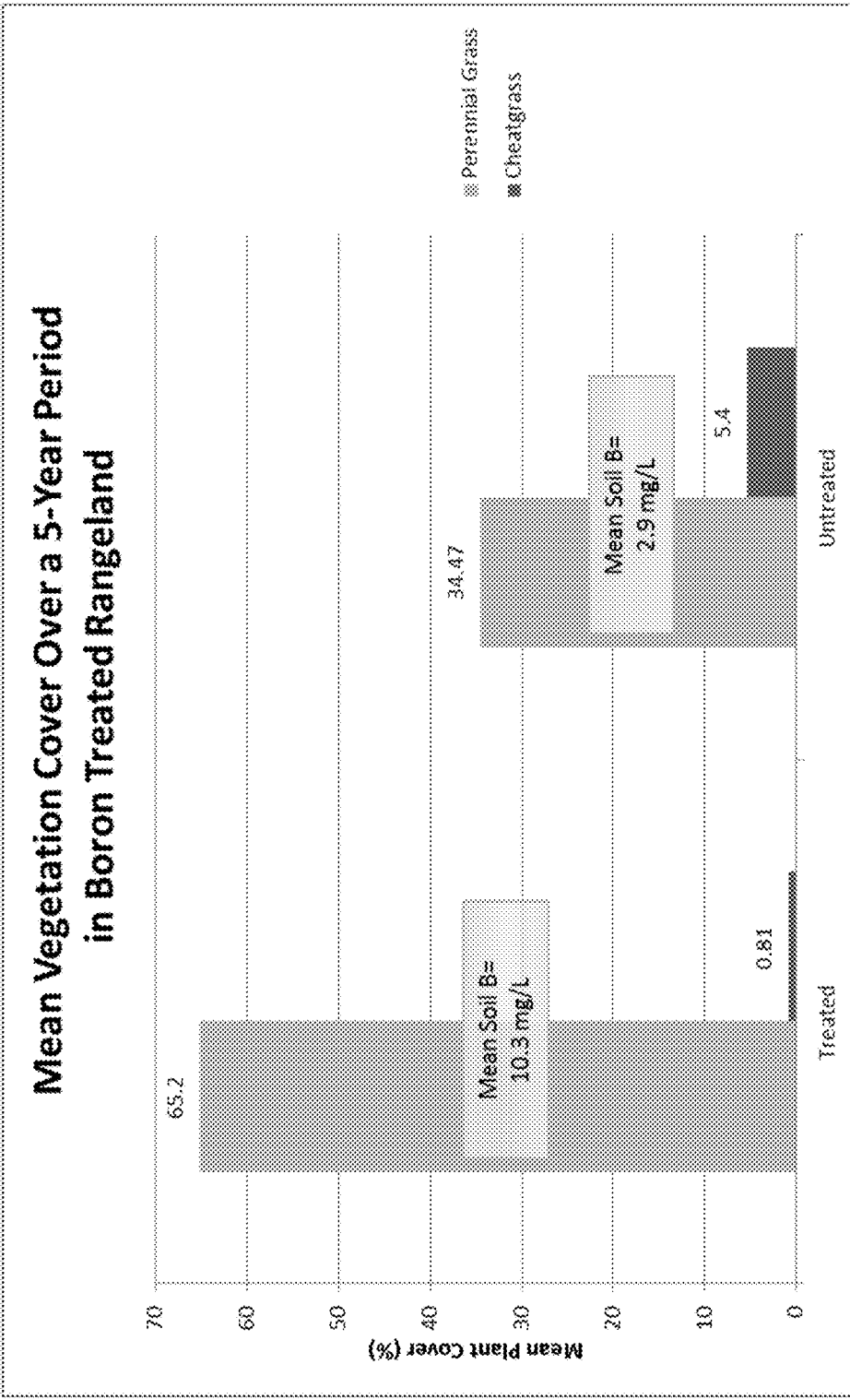
FIG. 5B illustrates rangeland site cheatgrass (*Bromus tectorum*) percent plant cover over a five-year study period compared to perennial grass cover in treated (10.3 mg B/L) and untreated (2.9 mg B/L) areas.

At a cheatgrass-affected rangeland site plant cover over a two-year study period is shown in response to water soluble soil boron concentrations resulting from surface liquid boron applications. Perennial grass cover in the treated rangeland site was increased to between 60 and 70 percent cover while cheatgrass cover decreased and was less than 3% (FIG. 5A) while adjacent untreated rangeland had less perennial grass cover and more cheatgrass after 2 years. (Soil sampling of the 0-6 inch depth was performed annually over a five year period to determine the water soluble boron concentrations both in the treated and untreated areas (FIG. 5B). Transects were used to measure plant cover annually at sites co-located with soil sampling.

Example 6

Figure 6:
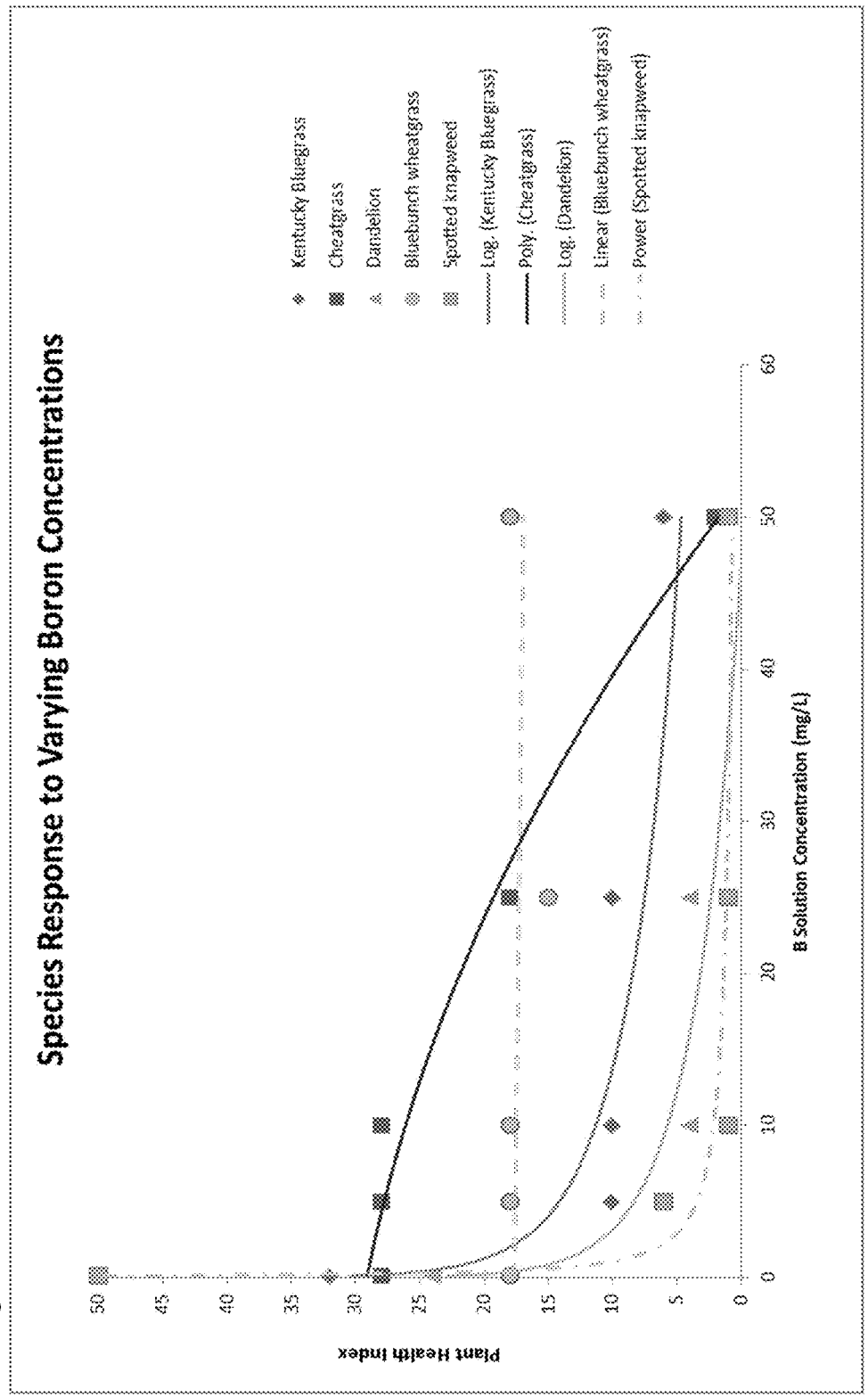
FIG. 6 illustrates the results of a greenhouse study of live cheatgrass (*Bromus tectorum*), dandelion (*Taraxacum officinale*), spotted knapweed (*Centaurea maculosa*), Kentucky bluegrass (*Poa pratenis*) and bluebunch wheatgrass (*Pseudoroegneria spicata*) plants in response to solutions of increasing boron concentration, as reflected in plant health index.

Plant color and vigor were measured in a small pot greenhouse study in response to solutions of increasing boron concentration, as reflected in a plant health index (same study as example 2 above). Bluebunch wheatgrass is a desirable native perennial grass common in rangeland of the western U.S. and a primary forage species of livestock and wildlife. Bluebunch exhibited little change in plant health with increasing boron concentrations while cheatgrass, dandelion, spotted knapweed and Kentucky bluegrass plants declined in vigor. Spotted knapweed showed the most rapid decline in plant health with increasing solution boron concentration. Spotted knapweed is commonly listed as a noxious weed by State agencies in the western U.S. Spotted knapweed commonly invades bluebunch wheatgrass plant communities in western Montana, and elsewhere in the western U.S. These results suggest micro-nutrient fertilization with boron solutions could be used to control spotted knapweed while allowing persistence of bluebunch wheatgrass. Greenhouse pot irrigation study, Bozeman, MT (FIG. 6).

Example 7

Figure 7:
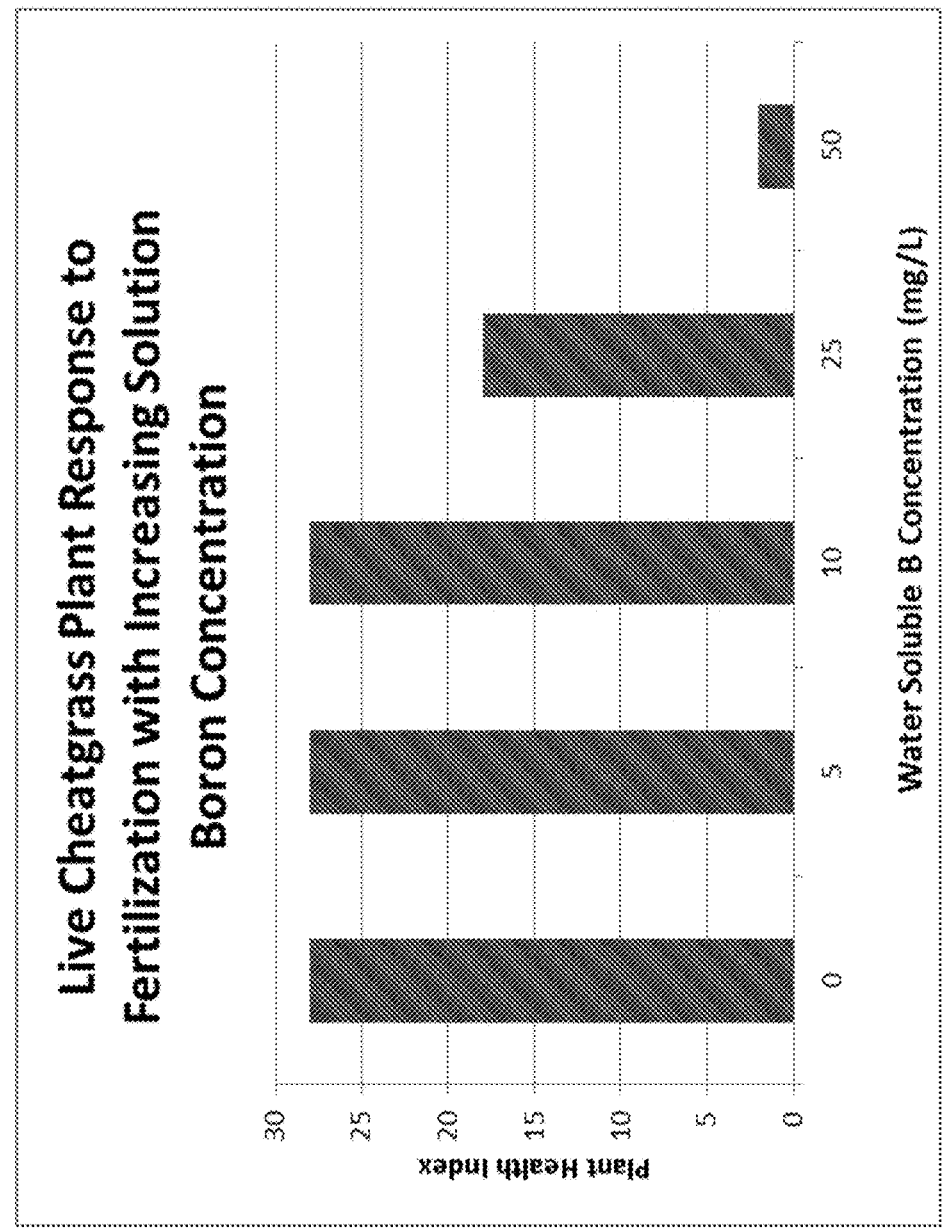
FIG. 7 illustrates live, near-mature cheatgrass plant responses, as measured by plant health index, to short-term application of various boron solutions. Solutions contain increasing concentrations of boron mixed with deionized water, compared to tap water.

Greenhouse evaluation of live/near-mature cheatgrass plant response to watering with increasing concentrations of boron-containing solutions, compared to watering with tap water (FIG. 7).

Seed initially germinated in potting soil watered with tap water for four months, after which watering with treatment solutions was initiated.

Pots watered with treatment solutions 3 times per week for two weeks, after which plant health index (product of qualitatively assessed plant color and vigor) was determined.

Example 8

Figure 8:
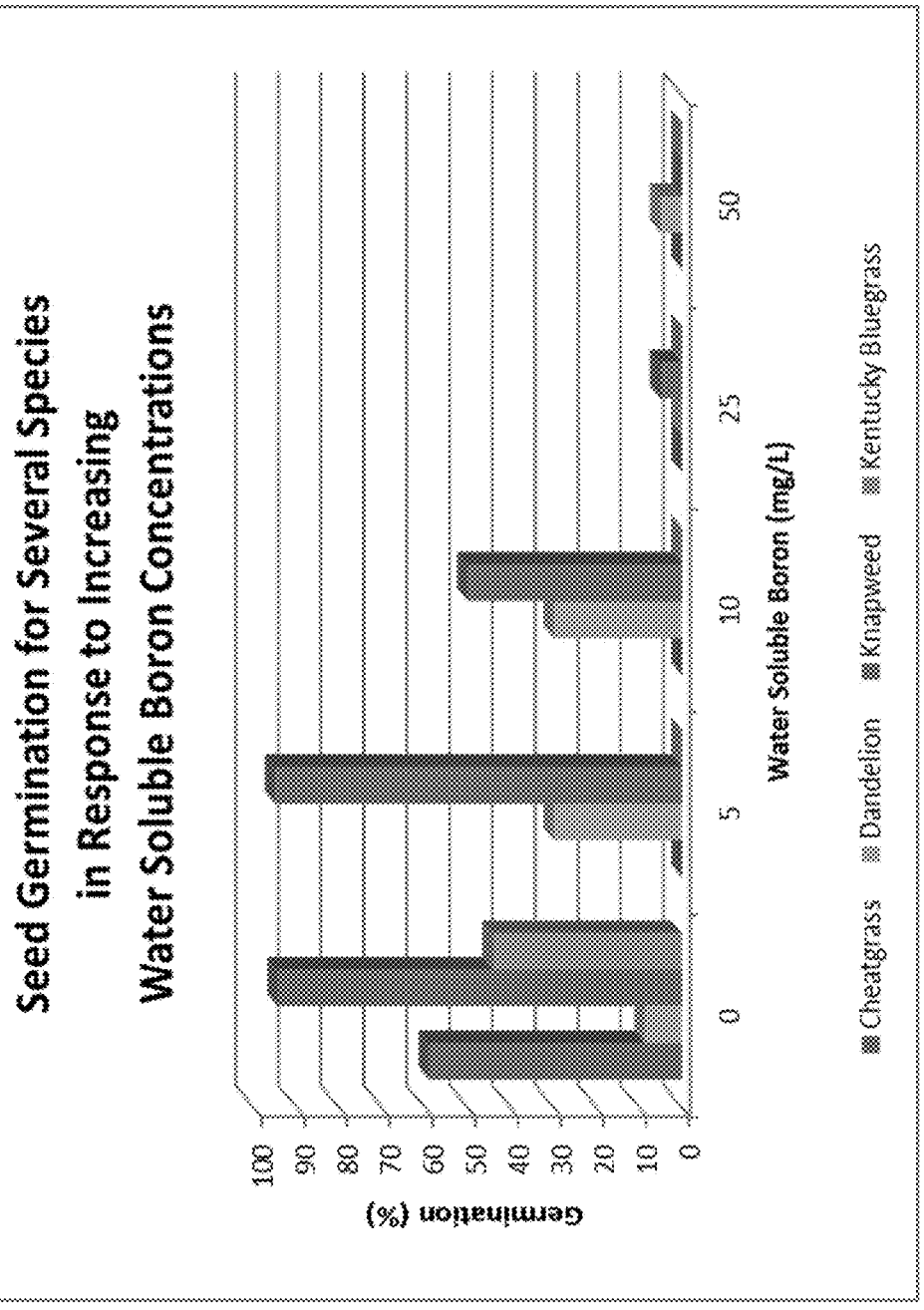
FIG. 8 illustrates percent germination of cheatgrass, dandelion, spotted knapweed and Kentucky bluegrass seed in a controlled benchtop (greenhouse) experiment ten (10) days post treatment of seed with solutions of increasing boron concentration.

Germination percentage of cheatgrass, dandelion, spotted knapweed and Kentucky bluegrass seed was measured ten (10) days after treatment with solutions of increasing boron concentration (FIG. 8). Cheatgrass appeared most sensitive to boron solution resulting in essentially 100% death of 20 cheatgrass seeds in covered petri dishes, when treated with solutions with boron concentration ranging from 5 to 50 mg/L. Control treatment using tap water successful germination percentage exceeded 56%.

Very little germination was observed by any species when boron concentrations reached 25 mg/L.

Example 9

In an illustrative example the micro-nutrient requirements for two unique species are shown: an invasive plant species and a desirable plant species. See FIG. 9.

The dose-response curves show plant deficiency at low concentration, maximum plant biomass production at unique moderate concentrations and phytotoxic species-specific responses at higher concentration. In this example, and based on supporting observations, invasive plant species have lower tolerance to elevated micro-nutrient levels. Each invasive species and desirable species is believed to have a unique micro-nutrient requirement, yet the invasive species may be controlled through micro-nutrient addition at the Induced Phytotoxicity Threshold (IPT) where the invasive species is reduced in vigor and distribution while the desirable species is unharmed or even stimulated by a beneficial micro-nutrient fertilization response. The short-term land management objective is to swiftly eradicate invasive plant species. The long-term land management objective in this plant-soil system is to restore and sustain micro-nutrient levels at the Induced Phytotoxic Threshold by balancing micro-nutrient inputs with withdrawals to maintain a long-term equilibrium micronutrient level phytotoxic to invasive plant species. It is believed that disequilibrium has been caused to many plant-soil systems by decreasing the levels of soil micro-nutrients through anthropogenic land management practices resulting in a net removal of soil micronutrients leading to increased susceptibility to invasive species colonization. In this invention, soil micro-nutrient levels are restored to pre-disturbance levels and soil health is reinvigorated leading to promotion of the desired plant species and minimization of the presence of invasive plant species.

Example 10

Formulation examples for invasive plant species (cheatgrass) as controlled by micronutrient (boron):

Formulation A, rate 1: dry granular boron-containing component 0.005882% by weight, water 99.99412% by weight. Thoroughly mix until completely dissolved, apply to target area containing mature cheatgrass, cheatgrass seedlings, or cheatgrass seed. This formulation can also be applied to a target area as a dry formulation, without mixing with water, and allowed to dissolve naturally through environmental conditions (precipitation) for uptake by cheatgrass plants, seedlings or seeds.

Formulation B, rate 1: dry granular boron-containing component 0.006666% by weight, water 99.99333% by weight. Thoroughly mix until completely dissolved, apply to target area containing mature cheatgrass, cheatgrass seedlings, or cheatgrass seed. This formulation can also be applied to a target area as a dry formulation, without mixing with water, and allowed to dissolve naturally through environmental conditions (precipitation) for uptake by cheatgrass plants, seedlings or seeds.

Formulation C, rate 1: dry granular boron-containing component 0.007142% by weight, water 99.99286% by weight. Thoroughly mix until completely dissolved, apply to target area containing mature cheatgrass, cheatgrass seedlings, or cheatgrass seed. This formulation can also be applied to a target area as a dry formulation, without mixing with water, and allowed to dissolve naturally through environmental conditions (precipitation) for uptake by cheatgrass plants, seedlings or seeds.

Formulation D, Using the boron-containing compound $Na_2B_4O_7.10\,H_2O$, the 0.5 mg/L soil concentration applied in the field experiment described in Example 1 was attained by adding 2.55 grams per 100 square foot. The 50 mg/L soil concentration was attained by adding 255 grams per 100 square feet. These concentrations were applied either dry or by dissolving the boron-containing compound in water and then applied as a liquid to field plots. The resulting data are shown in FIGS. 1A and 1B.

Example 11

Exemplary formulations for the micronutrient, boron, are outlined in Example 10; however each formulation can be similarly made with the other micronutrients of this invention at a specified concentration to achieve the IPT for the selected invasive species.

Example 12

On disturbed land (which may include degraded rangeland, mine land, roadside, brownfield, logged land, etc) in much of the western US, cheatgrass has become a dominant species displacing desirable native vegetation. Using a helicopter, tractor or similar dispensing method a micronutrient formulation containing boron (alternative: copper, manganese, zinc, etc) can be applied to the soil surface during the period of August awaiting fall precipitation and germination. The amount of water soluble and plant available boron will vary depending on the site soil and invasive species present, but might be in the range of 0.35-14 pounds of plant available boron per acre (e.g. 2.4-98 pounds per acre of boron fertilizer containing 14.3% boron). Alternative formulations could be developed using copper, zinc, manganese, molybdenum, chlorine and iron.

Upon adequate rainfall the micronutrient fertilizer will be dissolved and enter the soil where cheatgrass seeds will be found on the soil surface or near the soil surface. Under conditions of adequate moisture and soil temperature the cheatgrass seeds will germinate and begin to grow using stored carbohydrates in the seed. It is known by those skilled in the art that above ground plant growth is matched by below ground root development. Encountering micronutrients in the soil as a result of surface application, the plant roots will take up the nutrients which disrupt normal plant growth resulting in death of the emerging seedling. This type of response normally occurs in September-October as cheatgrass is a winter annual plant (although, it could happen anytime there is soil moisture, heat, cheatgrass seed—not in the winter and not during the period of active plant growth). In the spring remaining cheatgrass seed in the soil will encounter phytotoxic concentrations of micronutrients and perish. The removal of the annual plant would allow for more soil resources to go toward existing desirable plant species (e.g. bluebunch wheatgrass, Western wheatgrass, Idaho fescue, big sagebrush) and allow for establishment of desirable plant species which naturally exhibit greater tolerance to soil micronutrients compared to annual weeds.

Following the procedure set forth herein, the expected end result will be greatly diminished cheatgrass cover and the greater establishment of more desirable species leading to better forage for livestock and wildlife. For example, cheatgrass cover prior to treatment might range from 5-25% cover while desirable perennial grass cover might range from 25-35% plant cover; following micronutrient application cheatgrass cover is anticipated to decrease to less than 1% cover while perennial grass cover increases to 40-60% plant cover. In this example the desirable forage available for livestock and wildlife would increase 37-41%.

Following this procedure should result in a near-permanent soil treatment provided nutrient cycling continues to occur through good rangeland stewardship (i.e., not allowing overgrazing). Maintenance of the desired outcome requires mass balance, i.e., the nutrients input must balance with nutrients removed.

Example 13

In another example, for a roadside where cheatgrass may become established during a road widening project, the State Department of Transportation would hire a contractor to apply a liquid formulation of micronutrient fertilizer using a backpack sprayer along the roadside to control cheatgrass invasion. The conventional practice typically used prior to this invention was to spray an indiscriminant vegetation elimination compound (e.g. Roundup) around the base of each roadside delineator to facilitate mowing. Using the conventional Roundup practice, where Roundup is applied, cheatgrass invasion would result the following year due to the disturbance (elimination of plant cover), assuming that a cheatgrass seed source is available. Alternatively, the use of the micronutrient soil treatment will eliminate the growth the cheatgrass and allow for reestablishment of other more desirable grass or other plant species either through natural recolonization or through reseeding.

In the case where the Departments of Transportation desire a zone clear of vegetation around each highway delineator, a higher rate of micronutrient fertilization (~10× normal cheatgrass suppression rates for rangeland) could be applied to cause long-term elimination of cheatgrass. This technique would be an alternative to using Roundup to eliminate all vegetation. Roundup has to be applied annually. Longer term protection from weed encroachment is likely with this micronutrient technique.

Example 14

Near an oil well pad in southern Wyoming the soil is disturbed during drilling and development of the well. Under permit the oil company is required to reclaim the site. In this example, weed management for cheatgrass is a significant problem for these types of sites. Micronutrient fertilization would be applied to restore soil health and prevent weed colonization. Using this method, a soil sample will be collected of a near-by undisturbed site with healthy vegetation. The soil levels of micronutrients will be measured by a laboratory. The levels of soil micronutrients will also be measured in the disturbed soil. A prescription may then be developed to apply amounts of boron, copper, zinc and manganese to the disturbed site to bring the micronutrient levels in the disturbed soil to or near the levels that are measured in the near-by undisturbed site. The site may then be seeded with native plant species appropriate to that location and concurrently fertilized with the soil micronutrient prescription, resulting in the return of healthy vegetation cover on the oil well pad site, absent weeds.

Example 15

In a Kentucky bluegrass lawn in Chicago dandelions have become well established but the landowner is disinclined to use 2-4D herbicidal control methods. A Copper-Boron-Nitrogen fertilizer would be applied to the lawn at rates harmful to dandelions yet beneficial to Kentucky bluegrass resulting in diminished dandelion cover (reduced from 60% cover to 15% cover over 4 years following a single application) and increased bluegrass growth and vigor.

Example 16

In the Bitterroot Valley of western Montana elk herds may be declining in number due to reduced forage availability caused by rangeland degradation by a perennial noxious weed—spotted knapweed. Nearby livestock grazing operations experience similar losses in production. Fields invaded by knapweed have been sprayed annually by a conservation-minded landowner at a cost of $300/acre/application. The landowner has tried several herbicidal treatments (such as 2-4-D and other traditional formulations) with varying success, but the central problem is that while the herbicide kills 100% of the knapweed it is applied to a new generation of plants that germinates from seed reserves in the soil (knapweed seed may survive for decades) or new seed is blown in from the neighbor's property. The landowner is frustrated at the high cost and recurring problems from noxious weeds.

In this example of the invention, after traditional herbicide application to kill the mature perennial plants, a micronutrient application of boron would be surface applied as dry fertilizer using a tractor and PTO mounted flail spreader. The boron application would be applied in September on a dry year (low natural precipitation) and no knapweed seed germination would be expected to be observed in the fall prior to winter. Snowfall and spring rain following the treatment would dissolve the micronutrient application which would result in elevated levels of boron in the upper layer of soil containing invasive species seed.

Resident knapweed seed would be expected to germinate the following May in response to soil temperature and moisture. The germinating seed would put down an incipient root and surface dicot leaves as the plant begins to become established. However, in this example, unlike prior generations, the young knapweed plant would encounter elevated boron levels in the surface soil which would be phytotoxic to its growth. A majority of the young knapweed plants would die (some may germinate given a potentially non-uniform application of the boron treatment). The existing perennial grass plants are deep rooted and tolerant of boron and would be unharmed. Prior to treatment, the boron levels in the soil were lower than desired for perennial grass production, so following treatment a beneficial plant growth response would occur on the site. The net result would be long-term protection of the land from spotted knapweed germination and establishment, reduced weed control costs, increased forage production, and more elk.

Example 17

In this example, in Western North Dakota leafy spurge, a noxious weed that is difficult to control due to its extensive underground root system, has become well established. Application of traditional herbicide to the above ground leaf surfaces is successful in controlling the growth of leafy spurge during the year of herbicide application. However, the plant routinely resprouts the following season from roots unharmed by the herbicide since the herbicide did not translocate to the roots. Recognizing the invasive plant strategy of aggressively competing for soil nutrients an application of nitrogen, copper and boron will be applied in April—early in the growing season. Heavy spring rain would dissolve the fertilizer which can then be taken up by the plant root system, which recognizes the nutrients yet has no physiological controls for limiting uptake of phytotoxic concentrations.

The application and following uptake by leafy spurge plants would result in harm to the leafy spurge, including death of many of the leafy spurge plants. Additionally the resulting soil surface will be phytotoxic to leafy spurge seeds.

The soil will be reseeded with native and introduced plant seeds tolerant of the elevated micronutrient levels (primarily grasses such as smooth brome, western wheatgrass and timothy).

After a period of years, the site would be reseeded with appropriate native and introduced forbs (such as blue flax, alsike clover and alfalfa) which while somewhat tolerant of elevated soil Boron/Copper the site would require 2 to 7 years of equilibration prior to reaching non-toxic levels for the native forbs. The leafy spurge meanwhile would fail to recolonize the site due to its seed sensitivity to the soil treatment and eventually due to a lack of nearby seed source.

Example 18

In this example a severely burned rangeland site has become colonized by invasive plants which have reproduced for several years, accumulating a substantial seed bank of invasive plant seed. In addition to losses of soil micronutrients, the soil organic matter was also lost due to the intense heat of the fire and with it the primary source of macronutrient nitrogen. U.S. Forest Service and Bureau of Land Management experience with similar sites suggest that reseeding with native grasses is often unsuccessful due to the low nutrient levels and intense competition for soil resources by invasive plants. Addition of nitrogen through fertilization only makes the invasive plants grow larger and having limited affect on the few desirable species present. In this future application of soil micronutrients, application is performed in two steps.

In the first step, boron fertilizer would be applied early in the spring prior to plant growth and at rates phytotoxic to invasive plants seeds, to established mature invasive plants and to young germinating invasive plants. The goal of the first step (step 1) is to greatly diminish the plant cover of invasive plant species and to kill many invasive plant seeds. In the fall of the same year the site would be reseeded (dormant fall seeding) with desirable native plant species (primarily perennial grasses such as bluebunch wheatgrass and Idaho fescue). At the time of fall seeding a soil sample would be collected to assess the macronutrient (N/P/K) and micronutrient (Cu/Zn/Mn/Mo/Fe/B/Cl) levels in the soil.

In the early spring of the second year step 2 would be implemented prior to germination of the desirable species seeded. Step 2 would consist of a second fertilization activity focused on restoring both macronutrient and micronutrient fertility levels consistent with the nutritional requirements of the desirable species and based on the soil sample collected the previous fall. For example, in the hypothetical soil the nitrogen requirement was 22 pounds of nitrate nitrogen per acre, the phosphorous requirement is zero, the potassium requirement is zero, the copper requirement is 7 pounds per acre, the molybdenum requirement is 2 pounds per acre and the boron requirement is 1 pound per acre.

The first step would be a boron-only fertilizer intent on sharply reducing invasive species, while the second step would be a broad spectrum fertilizer intent on promoting growth of desirable plant species.

Example 19

In this example an alfalfa field has become invaded by cheatgrass, an invasive shallow—rooted annual grass. Alfalfa is deep-rooted and a perennial plant with high phosphorous fertilizer requirements. Alfalfa is often tilled up every 5-10 years due to depletion of soil phosphorous. Surface application of phosphorous fertilizer is ineffective as it does not leach into the soil profile and must be tilled into the soil to be effective. Tillage, fertilization and reseeding of alfalfa are expensive and the quality of forage is made worse by the presence of cheatgrass and shortening the period of healthy production. In this example, we assume cheatgrass increased from a few percent cover in the first growing season to 30% cover in the third growing season—an unacceptable level.

To reduce or remove cheatgrass an application of boron fertilizer would be applied at a rate in the range of 0.35-14 pounds of plant available boron per acre. Application of boron fertilizer would occur in September after the first frost (i.e. alfalfa no longer growing) and coincident with the end of the irrigation season, yet before potential fall cheatgrass germination.

The expected outcome would be the removal of cheatgrass through phytotoxic response to soil boron when germinating. In the spring of the following year, nitrogen fertilization could be added to stimulate the alfalfa crop where previously if nitrogen fertilization was added it would have only benefitted the cheatgrass and led to increased cheatgrass biomass and seed production—exactly opposite of the desired outcome. Alfalfa production is restored and cheatgrass removed through timely micronutrient application.

Example 20

Sage grouse, a candidate for endangered species listing, is dependent on sagebrush habitat for survival. The preferred sagebrush habitat is a mixture of forbs, perennial grasses and shrubs—especially sagebrush. This diverse rangeland habitat provides both hiding cover and forage for sage grouse during its life cycle. However, the sagebrush habitat of the western U.S. has become degraded, less diverse and colonized by invasive species—particularly cheatgrass. The sage grouse species has sharply declined in number and habitat restoration has not occurred due to a lack of cost-effective control methods for cheatgrass across millions of acres.

In this example, sagebrush restoration may be performed by aerial application of micronutrient fertilizer in the range of 0.35-14 pounds of plant available boron per acre in August of the growing season prior to fall germination of cheatgrass. Subsequent to control of cheatgrass by micronutrient-induced phytotoxicity, the same rangeland sites would be aerial seeded with desirable native plant species. Recontamination of boron-treated rangeland sites by wind-blown cheatgrass seed would occur, yet cheatgrass seed would fail to germinate due to the persistence of phytotoxic levels of plant available boron in the surface soil. Conversely, desirable native plant species would germinate in the boron-treated soil due to their differential tolerance of soil boron.

In this example, large tracts of land could be treated efficiently resulting in long-term reduction in cheatgrass cover and recolonization of disturbed sites by desirable plant species. Recovery of the native vegetation would provide opportunities for sage grouse recovery. The recovery of the degraded rangeland would be perpetuated through land stewardship which safeguarded both the soil quality and rangeland health by emphasizing very low intensity grazing intent on recycling soil nutrients.

Example 21

In this example, a rangeland site has become colonized by three invasive species. From dose-response testing it can be determined that 2 of the invasive species can be controlled by boron fertilization while the third is tolerant of boron, but not zinc. Of the two boron-sensitive invasive plant species, one is intolerant to a soil solution level of 3 mg boron per liter, while the other is sensitive to 7 milligrams per liter. The zinc-sensitive invasive plant species shows 38% biomass reduction at 0.4 mg zinc per liter and 89% biomass reduction at 0.9 milligrams per liter.

A custom blended micronutrient fertilizer could therefore be prepared which when applied to the surface soil results in a plant available boron level of 7 mg per liter and 0.9 mg zinc per liter. The combined micronutrient formulation would exploit phytotoxic response of three different invasive species found on the same rangeland site. In the following growing season an observer would expect to find greatly reduced plant cover of all three invasive plants.

Example 22

Figure 10:
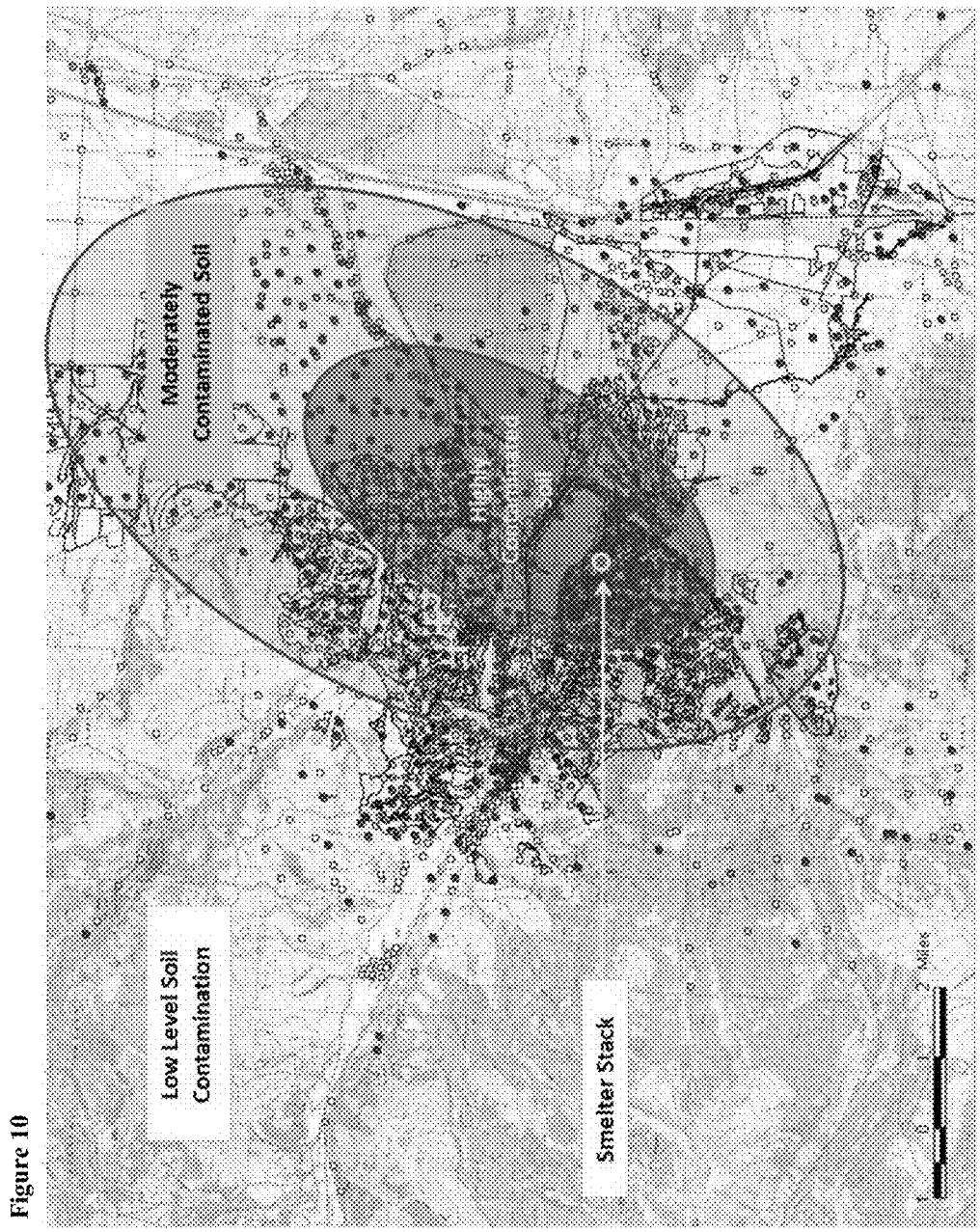
FIG. 10 illustrates the distribution of surface soil copper concentrations near a copper smelter. Each soil sampled is shown as a colored dot on the map. Red dots represent soils with the highest copper concentration, followed by yellow, then green. White dots represent the lowest concentrations. Plant community characteristics vary in relation to the degree of copper in soil (not shown). Plant community phytotoxicity is most pronounced in the highly contaminated soil near the smelter.
Figure 11:
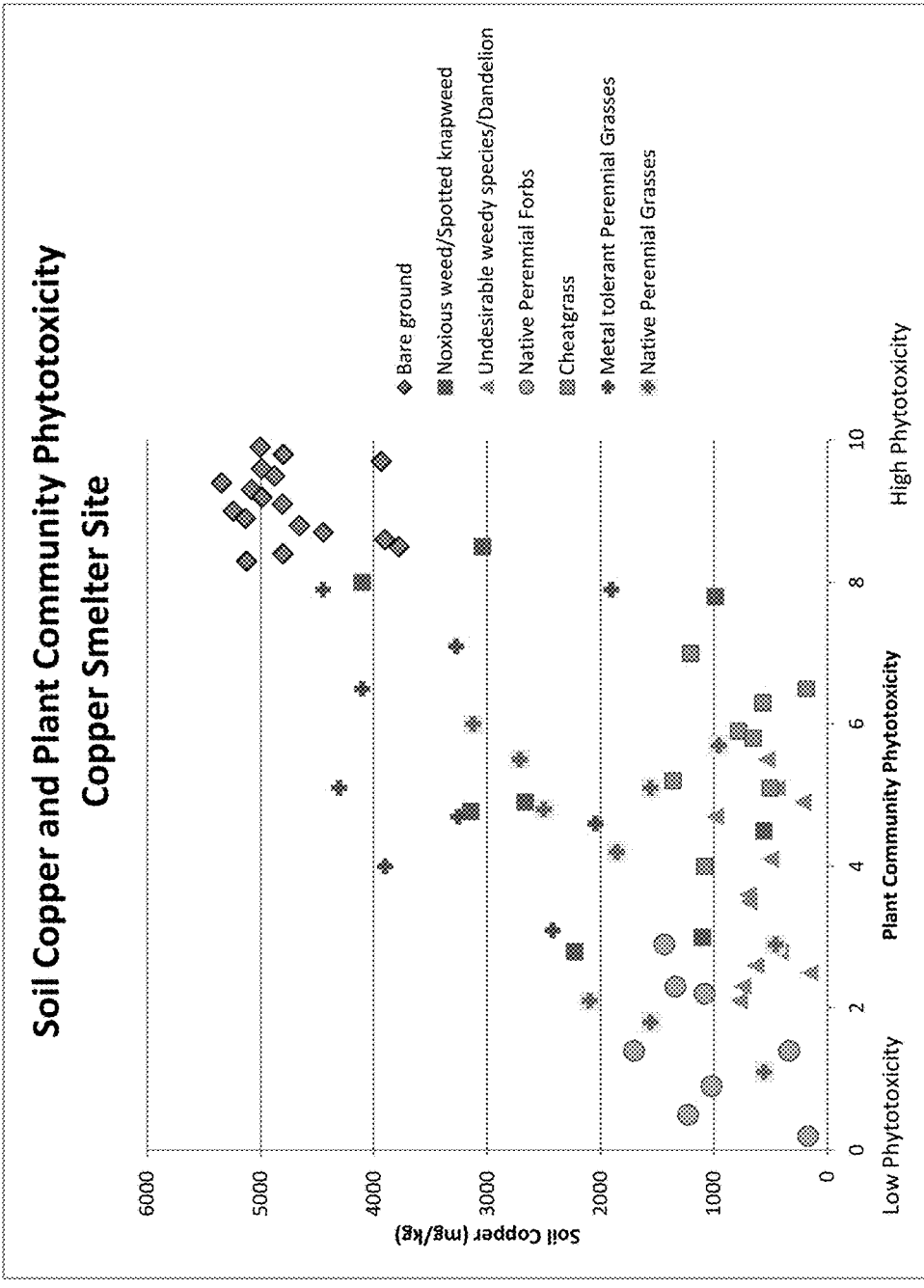
FIG. 11 illustrates the effect of copper soil contents on plant community phytotoxicity near the copper smelter site shown in FIG. 10. Plant community phytotoxicity is measured as a reduction in the aggregate assessment of the amount of plant cover, species diversity and prevalence of bare ground in response to increased copper levels. Individual species show differential sensitivity to the amount of soil copper. As soil copper levels increase fewer species are able to tolerate the higher concentrations. Total elemental levels of soil copper are shown as an index for plant-available levels which vary in complex patterns and especially related to soil pH.

In this example plant community health and diversity was surveyed in an area contaminated with copper from a nearby copper smelter site (FIG. 10). The prevalence of various invasive species including cheatgrass, dandelions, and perennial noxious weeds (forbs) was observed and correlated with soil copper contamination levels measured at various sites. The resulting phytoxicity correlations were synthesized from years of empirical observation with exemplary species having been selected to provide an overall picture of the types of vegetation observed at the sites (FIG. 11).

Figure 12:
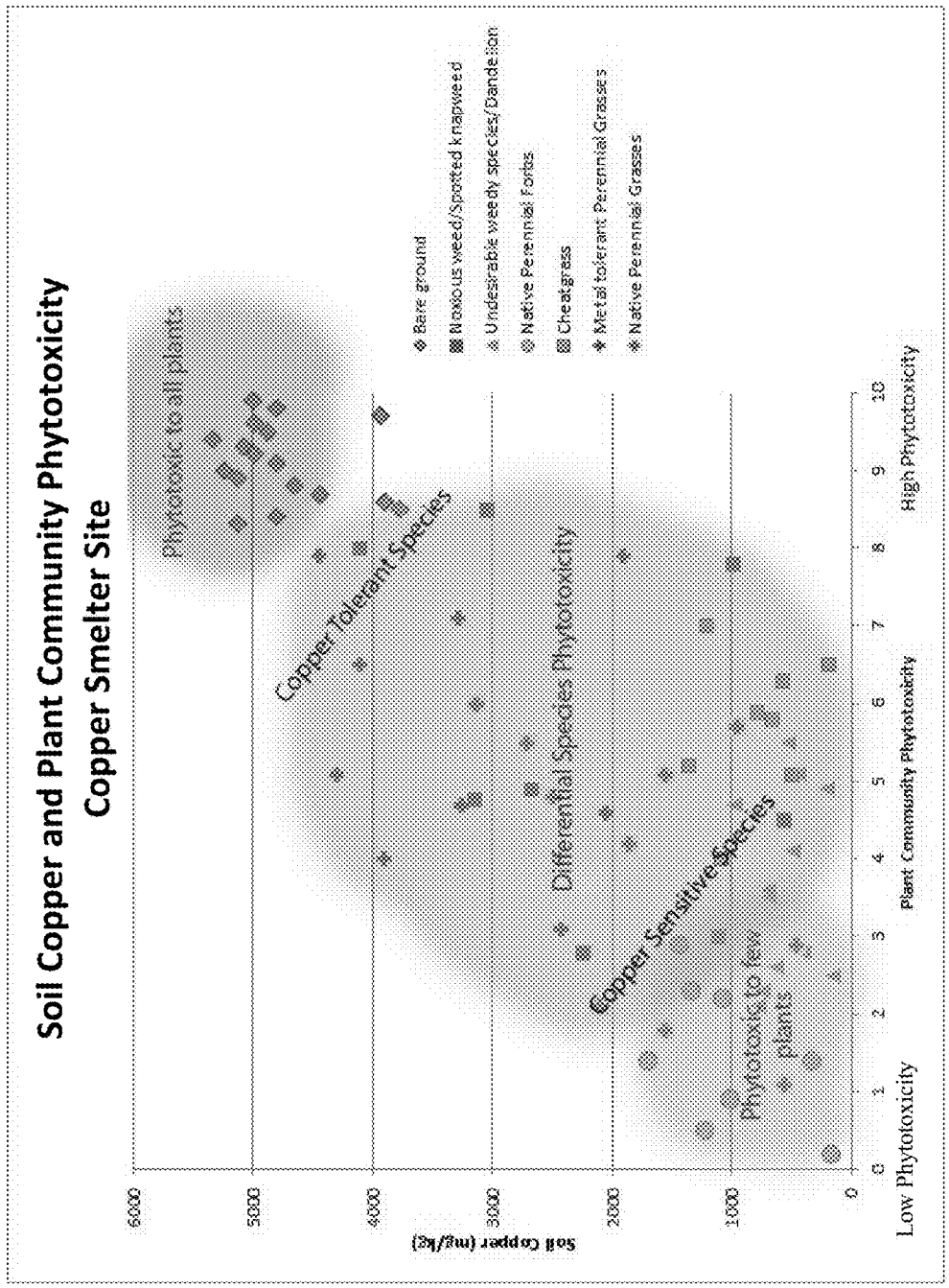
FIG. 12 differential zones of sensitivity to soil copper are depicted. In areas with high soil contamination, several plant types are not observed. Their absence is attributed to elevated soil copper. Dandelions, cheatgrass and native perennial forbs are locally extirpated from highly contaminated soil areas where these same areas support growth of metal tolerant grasses and noxious weeds. These spatial patterns of vegetation observed on the contaminated soil resulted from an uncontrolled release of metals from a copper smelter.
Figure 13:
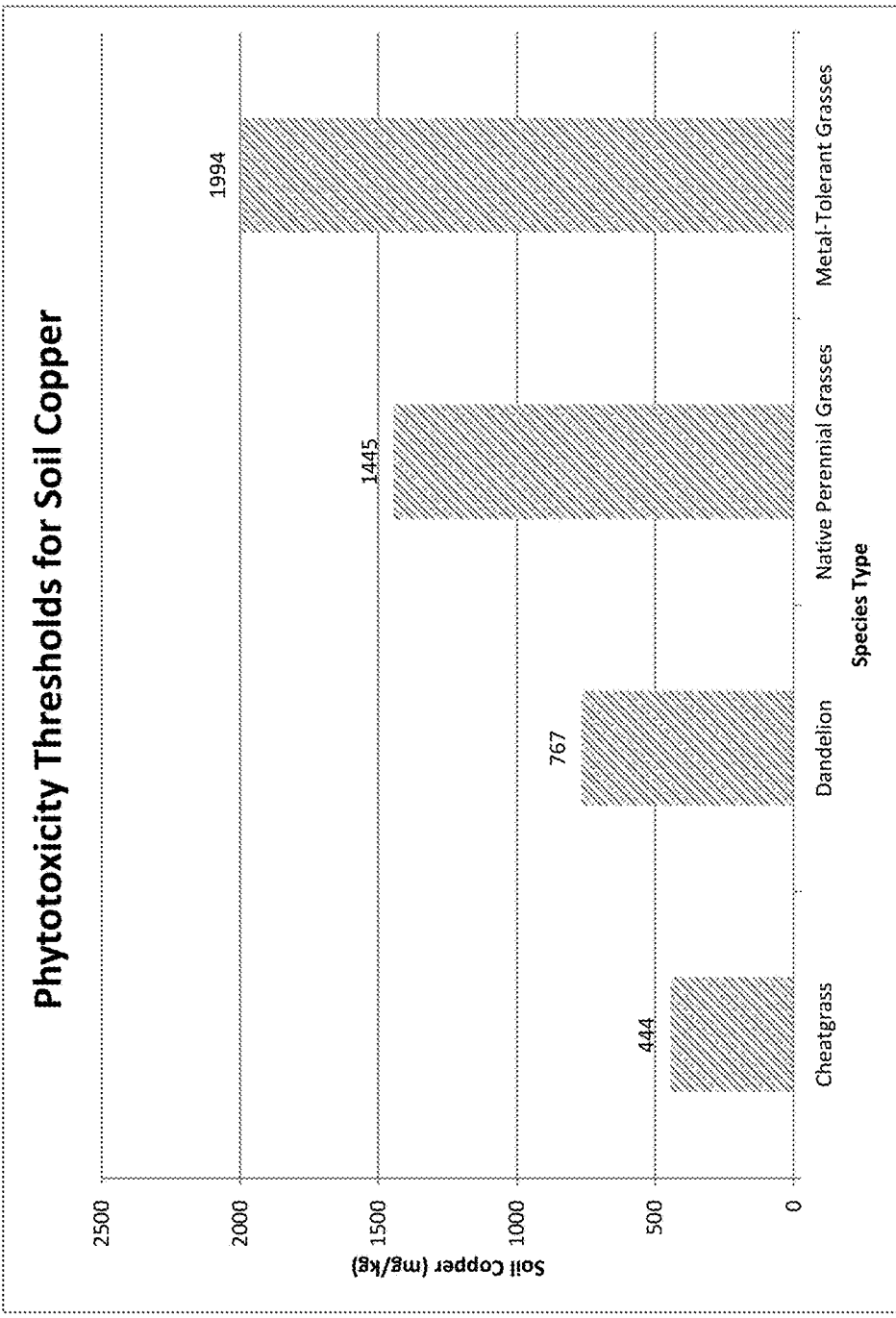
FIG. 13 phytotoxicity thresholds for cheatgrass, dandelions, perennial grass communities and metal-tolerant grasses. Thresholds calculated from aggregate assessments of the amount of plant cover, wherein less than 25% of the species type will persist when soil copper concentrations exceed the phytotoxicity threshold.

Invasive species were primarily observed at lower copper contamination sites whereas desirable native perennial grasses were found to tolerate higher copper soil levels (FIG. 12). The observations from these correlations can be summarized into copper phytoxicity threshold values wherein altering the amount of copper concentrations in the soil through application of copper or copper-containing compounds can influence vegetation growth (FIG. 13).

In some embodiments of the present invention, copper applications can be used to control the growth of invasive species such as cheatgrass and dandelion while preserving the growth of perennial grass and metal-tolerant grass species. In some embodiments copper applications to achieve concentrations higher than about 250 milligrams per kilograms of soil to about 1400 mg/Kg could be effective at controlling cheatgrass and dandelions in perennial grass communities. In other embodiments copper applications to achieve concentrations higher than about 250 to 1000 milligrams per Kg of soil are desired.

In other embodiments copper applications to achieve soluble copper concentrations of about 0.1 to 10 milligrams per liter of soil are desired.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

It is understood that there are other embodiments of the invention other than that described herein, which is provided to explain the invention to those skilled in the state of the art and should not be construed as limiting the claims made below.

ADDITIONAL REFERENCES

Bangsund, D. A., and Leistritz, F. L. 1991. Economic impacts of leafy spurge on grazing lands in the northern Great Plains. NDSU Agriculture Economic Report No. 275-S.

Elliott, G. C. and P. V, Nelson. 1981. Acute boron toxicity in Begonia×hiemalis Schwabenland Red.' Commun. Soil Sci. Plant Annu. 12(8):775-783.

Gogue, G. J. and K. C. Sanderson. 1973. Boron toxicity of Chrysanthemum. HortScience 8:473-475.

Hammer, P. A. and D. A. Bailey. 1987. Poinsettia tolerance of molybdenum. HortScience 22: 1284-1285.

Heap I. 2006. *The International Survey of Herbicide Resistant Weeds*. Available from URL: http://www.weedscience.com.

Jong-Myung, Chun-Ho Pak, and Chiwon W. Lee, 1996. Micro-nutrient toxicity in French marigold. J. Plant Nut. 19(6): 901-916.

Kabata-Pendias, A. and H. Pendias. 2001. Trace Elements in Soils and Plants, Third Edition. CRC Press.

Keren R and Bingham F T 1985 Boron in water, soils, and plants. Adv. Soil Sci. 1, 230-276.

Lee, Chiwon W., Jong-Myung Choi, and Chun-Ho Pak. 1996. Micronutrient Toxicity in Seed Geranium (*Pelargonium×hortorum* Bailey). J. Amer. Soc. Hort. Sci. 121 (1):77-82.

Marousky, F. J. 1981. Symptomology of fluoride and boron injury in *Lilium longiflorum* Thunb. J. Amer. Soc. Hort. Sci. 106:341-344.

Maxwell B. D., Roush M. L. and Radosevich S. R. 1990. Predicting the evolution and dynamics of herbicide resistance in weed populations. *Weed Technol.* 4, 2-13.

Pimentel, D., McNair, S., Janecka, J., Wightman, J., Simmonds, C., O'Connell, C., Wong, E., Russel, L., Zern, J., Aquino, T. and Tsomondo, T. 2001. Economic and environmental threats of alien plant, animal, and microbe invasions. Agriculture, Ecosystems and Environment 84: 1-20

Pimentel, D., Zuniga, R., and Morrison, D. 2005. Update on the environmental and economic costs associated with alien-invasive species in the United States. Ecological Economics. 52: 273-288.

Yamada, T., R. J. Kremer, P. R. de Camargo e Castro, and B. W. Wood. 2009. Glyphosate Interactions with physiology, nutrition, and diseases of plants: Threat to agricultural sustainability? Europ. J. Agron. 31:111-113.

The invention claimed is:

1. A method for selectively controlling growth of at least one invasive plant species existing in a perennial grass community, comprising: applying copper to an area including soil of the perennial grass community to achieve a soluble copper concentration in soil of the perennial grass community from about 0.1 milligrams per liter to about 50 milligrams per liter, and wherein said copper is phytotoxic to the at least one invasive plant species while preserving the growth and vigor of the perennial grass; wherein said at least one invasive plant species is dandelion.

2. The method of claim 1, wherein said copper produces a soluble soil copper concentration of about 0.1 milligrams per liter to about 5 milligrams per liter.

3. The method of claim 1, wherein the copper is a copper-containing compound.

4. The method of claim 1, wherein the area of the perennial grass community is a rangeland or disturbed land.

5. The method of claim 1, wherein the uppermost about 1 inch of the soil achieves a soluble copper concentration in the soil of the perennial grass community from about 0.1 milligrams per liter to about 50 milligrams per liter.

6. The method of claim 1, wherein the copper is applied to soil of the perennial grass community.

7. A method for negatively impacting the growth of at least one invasive plant species, comprising the selective control of the invasive plant species, existing in a perennial grass community rangeland, while preserving the perennial grass community species, comprising: applying copper to an area including soil of the perennial grass community to achieve a soluble copper concentration in soil of the perennial grass community from about 0.1 milligrams per liter to about 50 milligrams per liter in the uppermost about 1 inch of soil, and wherein said copper is phytotoxic to the at least one invasive plant species while preserving the growth and vigor of the perennial grass, wherein the at least one invasive species is dandelion.

8. The method of claim 7, wherein the copper is applied to soil of the perennial grass community.

* * * * *